(12) United States Patent
Voss et al.

(10) Patent No.: US 10,507,013 B2
(45) Date of Patent: Dec. 17, 2019

(54) CLOSURE DEVICES, SYSTEMS, AND METHODS

(71) Applicant: Abbott Cardiovascular Systems, Inc., Santa Clara, CA (US)

(72) Inventors: Laveille Kao Voss, Belmont, CA (US); Kelly A. Pike, Half Moon Bay, CA (US); David A. Mackiewicz, Scotts Valley, CA (US); Andrew Switky, Menlo Park, CA (US); Gina L. Romero, Los Altos, CA (US); Jonathan I. Kaplan, Palo Alto, CA (US); Anthony P. Patron, Mountain View, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 409 days.

(21) Appl. No.: 15/284,111

(22) Filed: Oct. 3, 2016

(65) Prior Publication Data
US 2017/0086805 A1    Mar. 30, 2017

Related U.S. Application Data

(62) Division of application No. 13/442,432, filed on Apr. 9, 2012, now Pat. No. 9,456,814.

(51) Int. Cl.
*A61B 17/00* (2006.01)

(52) U.S. Cl.
CPC ............... *A61B 17/0057* (2013.01); *A61B 2017/00623* (2013.01); *A61B 2017/00659* (2013.01); *A61B 2017/00668* (2013.01); *A61B 2017/00778* (2013.01); *A61B 2017/00867* (2013.01); *A61B 2017/00871* (2013.01)

(58) Field of Classification Search
CPC .......... A61B 17/0057; A61B 17/32075; A61B 17/12022; A61B 17/12036; A61B 17/1204; A61B 17/12118; A61B 2017/00778; A61B 2017/00668
See application file for complete search history.

(56) References Cited

U.S. PATENT DOCUMENTS

| 3,320,957 A | 5/1967 | Sokolik |
| 5,282,484 A | 2/1994 | Reger |

(Continued)

OTHER PUBLICATIONS

U.S. Appl. No. 14/928,950, Sep. 26, 2017, Office Action.

(Continued)

*Primary Examiner* — Sarah A Simpson
(74) *Attorney, Agent, or Firm* — Workman Nydegger; Randy Shen

(57) ABSTRACT

An anchor assembly configured to locate and anchor body tissue surrounding an opening in the body tissue. The anchor assembly can include a plurality of anchor elements. Each anchor element can include an elongate portion and an anchor portion extending from the elongate portion. The elongate portion can be configured to be manipulated by a user. The anchor portion can have a contracted configuration capable of passing through the opening in the body tissue and can have an expanded configuration capable of anchoring the body tissue surrounding the opening. The anchor portion and the elongate portion can be integrally formed from a single wire.

16 Claims, 17 Drawing Sheets

(56) References Cited

U.S. PATENT DOCUMENTS

| | | |
|---|---|---|
| 5,755,727 A | 5/1998 | Kontos |
| 6,558,349 B1 | 5/2003 | Kirkman |
| 6,623,510 B2 | 9/2003 | Carley et al. |
| 6,749,621 B2 | 6/2004 | Pantages et al. |
| 7,267,679 B2 | 9/2007 | McGuckin, Jr. et al. |
| 7,563,273 B2 | 7/2009 | Goldfarb et al. |
| 7,569,066 B2 | 8/2009 | Gerberding et al. |
| 7,854,810 B2 | 12/2010 | Carley et al. |
| 7,905,900 B2 | 3/2011 | Palermo et al. |
| 8,048,108 B2 | 11/2011 | Sibbitt, Jr. et al. |
| 8,398,677 B2 | 3/2013 | LaFontaine et al. |
| 8,469,994 B2 | 6/2013 | LaFontaine et al. |
| 8,579,932 B2 | 11/2013 | Pantages et al. |
| 8,672,953 B2 | 3/2014 | Reyes et al. |
| 8,920,442 B2 | 12/2014 | Sibbitt, Jr. et al. |
| 9,149,276 B2 | 10/2015 | Voss |
| 9,173,644 B2 | 11/2015 | Voss |
| 9,345,460 B2 | 5/2016 | Houser et al. |
| 9,456,814 B2 | 10/2016 | Voss et al. |
| 2003/0093096 A1 | 5/2003 | McGuckin et al. |
| 2004/0073242 A1 | 4/2004 | Chanduszko |
| 2004/0092973 A1 | 5/2004 | Chanduszko et al. |
| 2004/0158309 A1 | 8/2004 | Wachter et al. |
| 2004/0167570 A1 | 8/2004 | Pantages et al. |
| 2005/0038500 A1 | 2/2005 | Boylan et al. |
| 2006/0287674 A1 | 12/2006 | Ginn et al. |
| 2007/0276488 A1 | 11/2007 | Wachter et al. |
| 2008/0262541 A1 | 10/2008 | Sater et al. |
| 2008/0312667 A1 | 12/2008 | Drasler et al. |
| 2008/0312686 A1* | 12/2008 | Ellingwood ....... A61B 17/0057 606/219 |
| 2008/0312740 A1 | 12/2008 | Wachter et al. |
| 2010/0179567 A1 | 7/2010 | Voss et al. |
| 2010/0179571 A1* | 7/2010 | Voss .................. A61B 17/0057 606/142 |
| 2011/0066167 A1 | 3/2011 | Harris et al. |
| 2011/0144437 A1 | 6/2011 | Ortiz et al. |

OTHER PUBLICATIONS

U.S. Appl. No. 14/928,950, Mar. 30, 2018, Office Action.
U.S. Appl. No. 14/928,950, Jun. 4, 2018, Interview Summary.
U.S. Appl. No. 14/928,950, filed Oct. 30, 2015, Voss.
U.S. Appl. No. 12/684,400, Feb. 13, 2012, Office Action.
U.S. Appl. No. 12/684,400, May 9, 2012, Office Action.
U.S. Appl. No. 12/684,400, Oct. 16, 2012, Office Action.
U.S. Appl. No. 12/684,400, Feb. 23, 2015, Office Action.
U.S. Appl. No. 12/684,400, Jul. 28, 2015, Notice of Allowance.
U.S. Appl. No. 13/442,432, Oct. 30, 2013, Office Action.
U.S. Appl. No. 13/442,432, Dec. 26, 2013, Office Action.
U.S. Appl. No. 13/442,432, Apr. 9, 2014, Office Action.
U.S. Appl. No. 13/442,432, Jun. 19, 2014, Advisory Action.
U.S. Appl. No. 13/442,432, Oct. 15, 2014, Office Action.
U.S. Appl. No. 13/442,432, May 27, 2015, Office Action.
U.S. Appl. No. 13/442,432, Jan. 29, 2016, Office Action.
U.S. Appl. No. 13/442,432, May 20, 2016, Notice of Allowance.

* cited by examiner

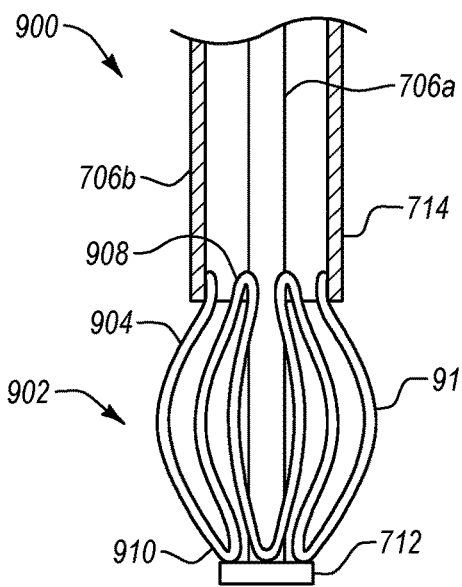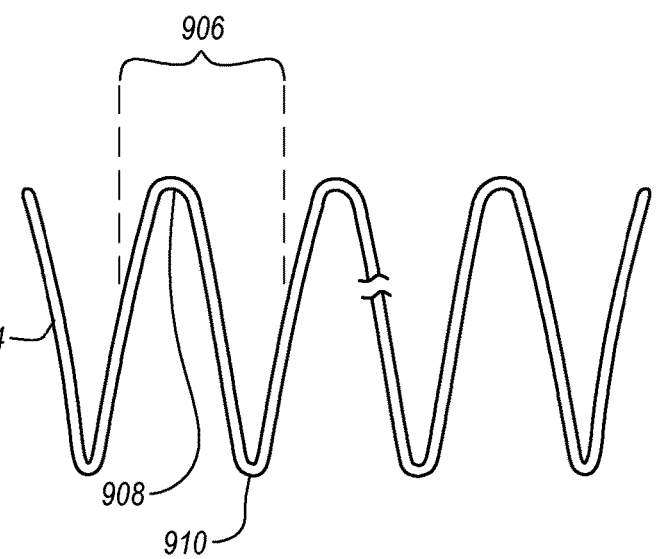
Fig. 9A                                    Fig. 9B
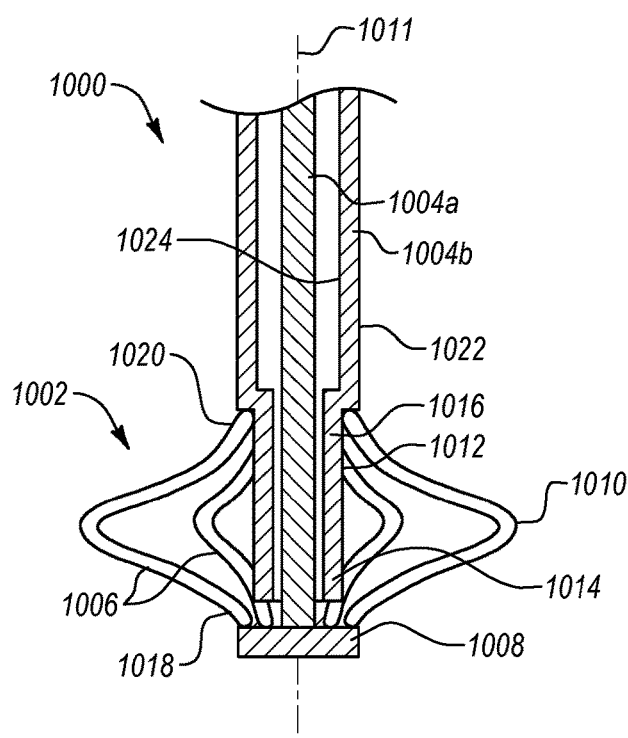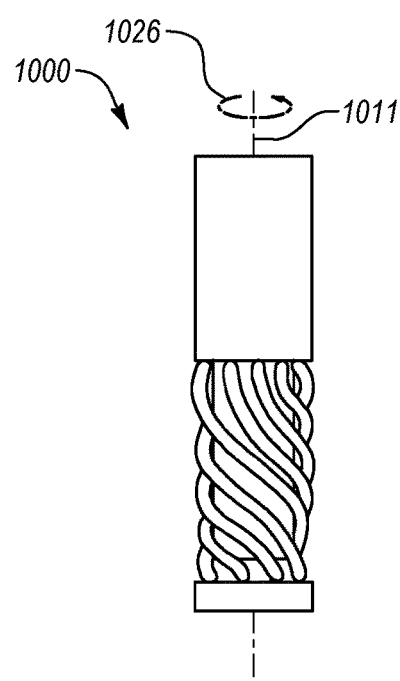
Fig. 10A                                   Fig. 10B

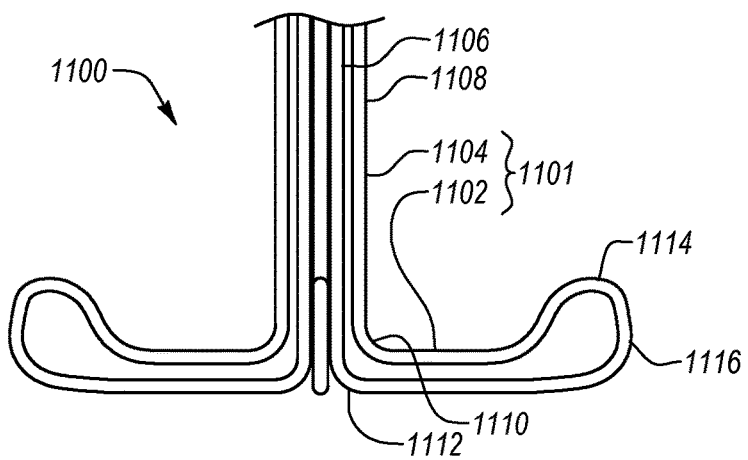
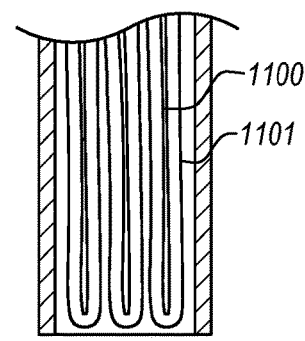
Fig. 11A
Fig. 11C
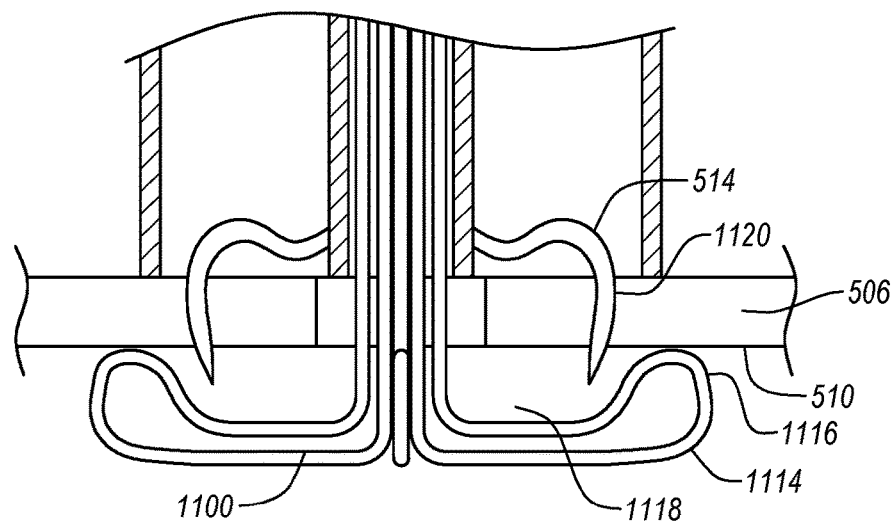
Fig. 11B

CLOSURE DEVICES, SYSTEMS, AND METHODS

CROSS-REFERENCE TO RELATED APPLICATIONS

This application is a divisional of U.S. application Ser. No. 13/442,432, filed Apr. 9, 2012, the disclosure of which is incorporated in its entirety by reference herein.

BACKGROUND OF THE INVENTION

1. The Field of the Invention

The present disclosure relates generally to medical devices and corresponding methods of use. In particular, the present disclosure relates to vessel closure systems and devices and corresponding methods of use.

2. The Relevant Technology

During intravascular and other related medical procedures, catheters are typically inserted through an incision or puncture in the skin and underlying tissues to access an artery or vein, typically in the groin, neck, or subclavian areas of a patient. The catheter can be inserted through a puncture in the blood vessel and guided to the desired site to perform interventional procedures such as angiography, angioplasty, stent delivery, plaque removal, and infusion of a therapeutic substance.

Often these procedures are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. The catheter typically is passed through the lumen of the introducer sheath and advanced over the guide wire into position for the medical procedure.

After the procedure is completed and the catheter and introducer sheath are removed from the patient, however, the access hole must be closed to prevent hemorrhage. This is typically achieved by applying pressure over the blood vessel manually and then by applying a pressure bandage or a compressive weight. With conventional methods, the rate of post-puncture hemorrhage is high, which can cause considerable complications. This impediment is exacerbated by the concomitant use of anticoagulant medications such as heparin or warfarin and by anti-platelet drugs, which are commonly used following a procedure in order to prevent clot formation and thrombus and/or to treat vascular disease.

It is generally recognized that many currently employed vascular sealing methods and devices and other tissue closure methods and devices incompletely seal holes or wounds in vascular or other tissue. Achieving complete wound closure is particularly important in sealing arterial punctures, which are relatively high pressure systems. For example, under normal blood pressure, the arterial system has a pressure of about 104/80 mmHg or more. Failure to completely close arterial holes can result in hematoma, exsanguination, and other catastrophic consequences, including limb amputation and death.

BRIEF SUMMARY

The present disclosure includes anchor assemblies configured to locate and/or anchor tissue surrounding a body lumen opening. In one implementation, the anchor assembly can include a plurality of anchor elements. Each anchor element can include an elongate portion configured to be manipulated by a user and an anchor portion extending from the elongate portion. The anchor portion can have a contracted configuration capable of passing through a body tissue opening and an expanded configuration capable of anchoring tissue surrounding the body tissue opening. The anchor portion and elongate portion can be integrally formed from a single wire. In one implementation, the wire of each anchor element can have a diameter between about 127 µm and about 178 µm. The anchor assembly can be comprised of a shape memory material.

In one implementation, the plurality of anchor elements can comprise at least eight anchor elements. In one implementation, in the expanded configuration each anchor portion can extend radially outward from a longitudinal axis of the anchor assembly, the radial direction being different for each anchor portion. In one implementation, each anchor portion can extend substantially orthogonally outward from the corresponding elongate portion in the expanded configuration. In one embodiment, each anchor portion can form an acute angle with respect to its corresponding elongate portion in the expanded configuration. In a further implementation, the acute angle can be between about 10 degrees and about 75 degrees.

In one implementation, each anchor portion can include a first section that extends from the corresponding elongate portion and a second section that extends from the first section. In a further implementation, in the expanded configuration the first section can form an acute angle with respect to the elongate portion, and the second section can be substantially orthogonal to the elongate portion. In a further implementation, the second section can extend from the first section towards the elongate portion.

In one implementation, each elongate portion can comprise both of the opposite ends of a single wire and each anchor portion can comprise a middle portion of the wire extending between the opposite ends. In a further implementation, the anchor portion of the wire can comprise a loop section that extends proximally with respect to a non-looped section of the anchor portion.

In one implementation, the anchor assembly can include an elongate portion configured to be manipulated by a user and a plurality of anchor portions. The elongate portion can include a first elongate member disposed through a generally tubular second elongate member. The anchor portions can each have a contracted configuration capable of passing through a body tissue opening and an expanded configuration capable of anchoring tissue surrounding the body tissue opening. In one implementation, the wire of each anchor element can have a diameter between about 127 µm and about 178 µm.

In one implementation, the anchor portion and elongate portion can be integrally formed from a single wire. In one implementation, the anchor portions can be expanded and contracted by moving the first elongate member longitudinally with respect to the second elongate member. In one implementation, the anchor portions can be expanded and contracted by rotating the first elongate member with respect to the second elongate member. In one embodiment, the anchor assembly can be comprised of a shape memory material. In one implementation, each anchor portion can include a projection configured to be movable between a contracted configuration and an expanded configuration. In one implementation, each anchor portion can have a first contracted configuration, wherein the anchor portion can be retracted into the second elongate member, and a second contracted configuration, wherein the anchor portion can be elongated in a distal direction.

Implementations of the present disclosure can also include a closure system. In one implementation, the closure system can include a handle member, a tube set configured to deliver and deploy a closure element, a plunger member movably coupled to the handle member, and an anchor assembly disposed at least partially within the tube set. In one implementation, the anchor elements are configured to be withdrawn through the body lumen opening without causing significant damage to the tissue surrounding the body lumen opening. In one implementation, the anchor elements are configured to be withdrawn through the closure element without causing significant damage to the tissue surrounding the body lumen opening.

Implementations of the present disclosure can also include methods of closing an opening in a tissue wall. In one implementation, the method can include positioning a closure system adjacent to an opening in the tissue wall, the closure system including an anchor assembly and a closure element disposed within a tube set; deploying the anchor assembly from the tube set, the anchor assembly comprising one or more anchor elements having an anchor portion and an elongate portion, the anchor portion of each anchor element moving from an initial contracted configuration to a deployed expanded configuration upon deployment of the anchor assembly; positioning the anchor portion of each anchor element against a distal surface of the tissue wall proximate the opening; positioning a distal end of the tube set against a proximal surface of the tissue wall proximate the opening to sandwich the tissue wall proximate the opening between the anchor portions and the tube set; deploying the closure element from the closure system to close the opening in the vessel wall, the anchor portions of the anchor elements remaining positioned against the distal surface of the tissue wall during deployment of the closure element; retracting the anchor portions of the anchor elements back into the tube set; and removing the closure system from the closed opening.

In one implementation, positioning the closure system adjacent to the opening in the tissue wall can include inserting a portion of tube set through the opening. In one implementation, the distal end of the tube set can remain positioned against the proximal surface of the tissue wall during deployment of the closure element. In one implementation, the distal end of the tube set can remain positioned against the proximal surface of the tissue wall during retraction of the anchor portions back into the tube set. In one implementation, the anchor portions can be withdrawn through the closure element during retraction of the anchor portions back into the tube set. In one implementation, the anchor portion of each anchor element can move from the deployed expanded configuration back to the initial contracted configuration during retraction of the anchor portions back into the tube set.

These and other advantages and features of the present disclosure will become more fully apparent from the following description and appended claims, or may be learned by the practice of the disclosure as set forth hereinafter.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope. In the drawings, like numerals designate like elements. Furthermore, multiple instances of an element may each include separate letters appended to the element number. For example, two instances of a particular element "20" may be labeled as "20a" and "20b". In that case, the element label may be used without an appended letter (e.g., "20") to generally refer to every instance of the element; while the element label will include an appended letter (e.g., "20a") to refer to a specific instance of the element.

FIG. 9A is a partial cross sectional side view of another embodiment of an anchor assembly;

FIG. 9B is a side view of the anchor portion of FIG. 9A, expanded and flattened to show the structure thereof;

FIG. 10A is a cross sectional side view of another embodiment of an anchor assembly in the expanded configuration;

FIG. 10B is a side view of the anchor assembly of FIG. 10A in the contracted configuration;

FIG. 11A is a side view of another embodiment of an anchor assembly in the deployed position;

FIG. 11B is a partial cross sectional side view of the anchor assembly of FIG. 11A showing the positioning of the deployed anchor assembly in relation to a closure element during deployment; and FIG. 11C is a partial cross sectional side view of the anchor assembly of FIG. 11A in the retracted position.

DETAILED DESCRIPTION

Figure 1:
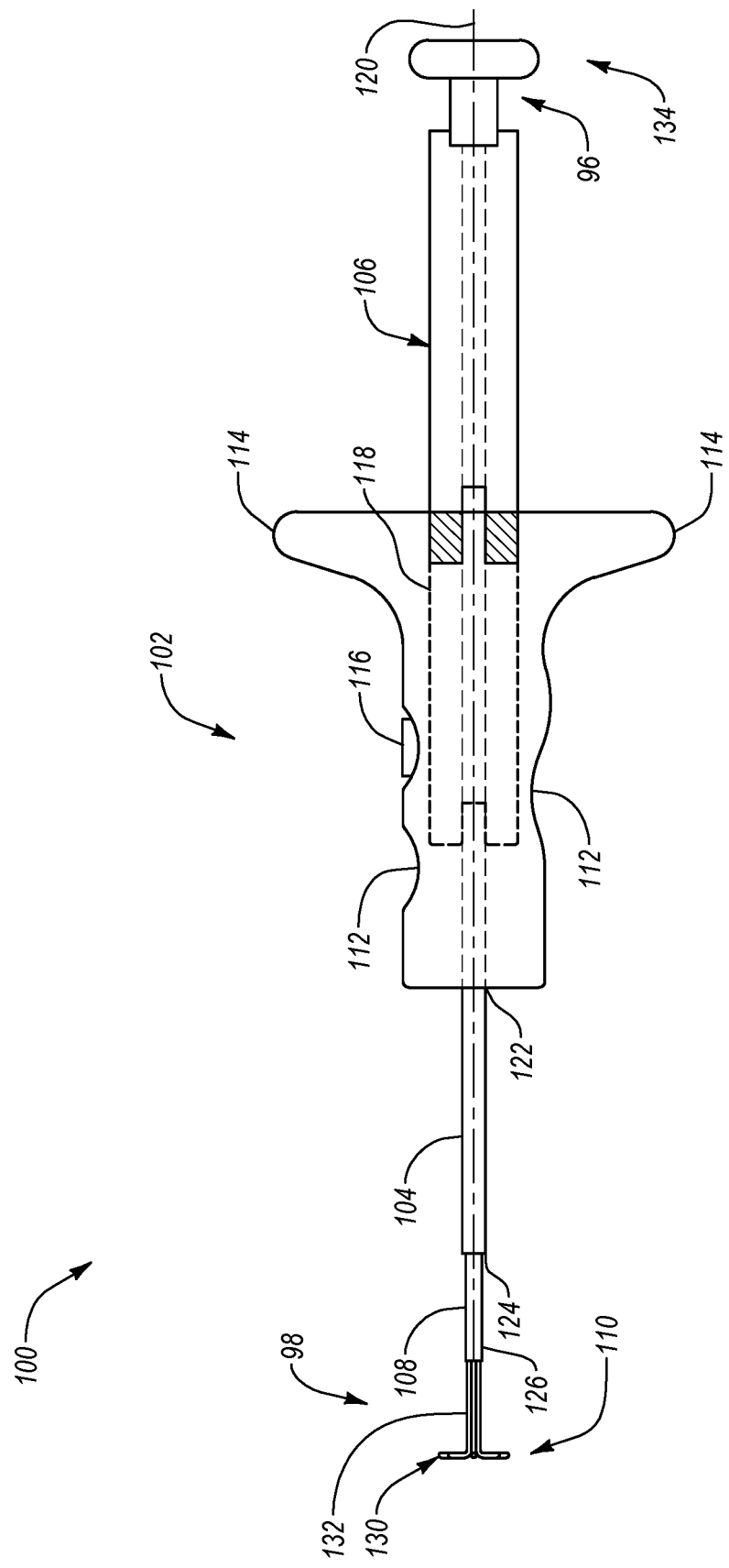
FIG. 1 is a side view of a tissue closure system according to one embodiment.

As used in the specification and appended claims, directional terms, such as "top," "bottom," "up," "down," "upper," "lower," "proximal," "distal," and the like are used herein solely to indicate relative directions in viewing the drawings and are not intended to limit the scope of the claims in any way.

The present disclosure provides methods and apparatuses that are suitable for closure of vascular punctures or other openings in bodily tissues. The devices and methods described herein are configured for wound closure on the external surface of the wound, which allows wound healing with little endothelial disruption thereby reducing the chances of intravascular thrombosis or embolism or intimal hyperplasia.

Generally, the apparatuses and methods described herein can be used with any type of body tissue that has sufficient strength to be held together by the tissue closure devices described hereinafter. By way of example only, embodiments of the present invention can be used to close openings in tissues that have a wall or membrane function, e.g, pulmonary, intestinal, vascular, urethral, gastric, renal or other wall structures, or in membranes, e.g., amniotic or pericardial membranes. Openings in other types of tissues can also be closed using embodiments of the present invention. Although many types of body tissue can be closed by the methods and apparatuses disclosed herein, the description included herein refers to "vessels" for convenience.

Furthermore, the apparatuses and methods described herein can be used with large and small hole punctures or other openings in the body tissue. By way of example, the tissue engaging devices of the present invention can be sized to close holes from 5 French to 30 French or larger. It may also be possible to close holes of other sizes.

The present disclosure relates to devices, systems, and methods for closing an opening in a body tissue. In one embodiment, a closure system may allow an operator to quickly and efficiently close a tissue opening while simultaneously providing the operator with a greater measure of control and flexibility in positioning and anchoring the closure system than previously available. For example, the closure system may allow an operator to achieve a more intimate securement of a closure element in the tissue surrounding the opening. In a yet further embodiment, the closure system may be compatible with a wider range of tissue wall thicknesses, thereby taking into account, e.g., the possibility of calcifications or scar tissue in the tissue wall. In addition, the closure system may be able to be advanced into the opening over a guidewire. Furthermore, the closure system may be compatible with a variety of sizes of body tissue openings and tissue tracts.

The present disclosure also relates to a device closure system with a removable anchor. In one embodiment, the anchor can be deployed from a contracted state to an expanded state. When in the expanded state, the anchor can be used to locate an opening in a tissue such as a vessel (e.g., an arteriotomy) when deploying, for example, a closure element, such as a clip or staple. The anchor, in conjunction with a tube set in the closure system, may sandwich the tissue surrounding the opening. This effectively locates the opening and aids in effective and proper deployment of the closure element.

The closure system may then retract or remove the anchor during use of the closure system, leaving the tissue opening at least substantially closed or sealed by the closure element. During removal, the anchor can deform without dislodging the closure element. More specifically in one embodiment, the anchor is withdrawn back into the tube set and into the pre-deployed state after the closure element has been deployed. Thus, the closure system can close an opening in a body tissue using a removable anchor.

Turning now to the drawings, FIG. 1 illustrates a closure system 100 in accordance with one embodiment. Closure system 100 is configured to close an opening in a body tissue, as discussed below. Closure system 100 extends between a proximal end 96 and a distal end 98 and includes a handle member 102, a tube set 104 coupled to the handle member 102, a plunger member 106, an inner cannula 108, and an anchor assembly 110 disposed at least partially within a lumen 111 (FIG. 4A) of inner cannula 108. An operator, such as a physician, may utilize closure system 100 and the elements thereof to close an opening in a body tissue.

For example, as will be explained in more detail below, plunger member 106 may be used to deploy anchor assembly 110 to locate the distal surface of a tissue wall and position closure system 100 relative to an opening in the tissue wall. Thereafter, handle member 102 and tube set 104 may be used to deliver a closure element, such as a clip or staple, and deploy the closure element into the tissue wall to close or substantially close the opening therein.

Handle member 102 is configured to assist an operator, such as a physician, to grip, manipulate, advance, and/or operate closure system 100 in order to close an opening in body tissue. In particular, handle member 102 may have a shape and size that conforms to the shape and size of a human hand. Handle member 102 may also include a number of indentations 112 configured to at least partially receive the fingers and/or thumbs of the operator. Indentations 112 may assist the operator to grip and manipulate handle member 102 and closure system 100. Handle member 102 may also include one or more flanges 114 to assist an operator to grip, advance, and/or retract handle member 102 and/or closure system 100.

Handle member 102 may also include any number of mechanisms necessary to deploy a closure element. For example, handle member 102 may include a button 116 operatively associated with one or more mechanisms configured to deploy a closure element. Button 116 may be positioned in or proximate to one of the indentations 112. In a further embodiment, button 116 may be operatively associated with one or more elements of tube set 104 configured to deploy a closure element. As a result, an operator may depress button 116 to push, fire, or eject a closure element from tube set 104 into the tissue to close an opening in the tissue.

In one embodiment, handle member 102 includes a recess 118 configured to receive at least a portion of plunger member 106. Recess 118 is configured to allow plunger member 106 to move in a longitudinal direction relative to handle member 102. In particular, recess 118 allows plunger member 106 to move both distally and proximally relative to handle member 102, along a longitudinal axis 120. For example, recess 118 may have a cross-sectional shape similar to, but slightly larger than, the cross sectional shape of plunger member 106. As a result, plunger member 106 may slide longitudinally into and out of recess 118 to move relative to handle member 102.

Handle member 102 may be comprised of any number of rigid or semi-rigid materials. For example, handle member 102 may be comprised of any number of polymers, plastics, metals, composites, other similar materials, or combinations thereof.

Tube set 104 is coupled to and/or partially disposed within handle member 102. Tube set 104 extends between a proximal end 122 coupled to handle member 102 and a distal end 124. Tube set 104 is configured to contain, deliver, and/or deploy a closure element. In particular, tube set 104 includes one or more tubular members and/or other mechanisms configured to house, advance, push, fire, and/or eject the closure element. For example, tube set 104 may include a pusher tube, a garage tube, a carrier tube, and/or other similar elements. In one embodiment, tube set 104 includes a spring-loaded pusher member configured to deploy the closure element when released or activated.

The closure element may be disposed within tube set 104 in an initial, open configuration and may be configured to be deployed from tube set 104 and move to a deployed, closed configuration, as discussed below. In particular, in one embodiment the closure element may store sufficient energy, while in its initial, open configuration, to engage the tissue and close an opening therein. For example, the closure element may include any of a number of shape memory and/or superelastic materials and may be set to elastically return to a deployed, closed configuration from any other configuration. In one embodiment, the closure element includes nitinol. The closure element may be a clip, a staple, or other type of closure element. Examples of closure elements that can be used in closure system 100 are disclosed in U.S. Pat. No. 6,623,510, issued Sep. 23, 2003 and U.S. Pat. No. 7,854,810, issued Dec. 21, 2010, the disclosures of which are incorporated by reference herein in their entirety.

Inner cannula 108 extends from distal end 124 of tube set 104 to a distal end 126. Anchor assembly 110 may be disposed at least partially within lumen 111 of inner cannula 108, and/or within tube set 104, handle member 102, and/or plunger member 106. In one embodiment, inner cannula 108 is movable longitudinally, such as slidable, with respect to tube set 104, handle member 102, and/or plunger member 106. As a result, inner cannula 108 may move either distally or proximally relative to tube set 104, handle member 102, and/or plunger member 106.

Inner cannula 108 is configured to house and deliver anchor assembly 110 to or away from an opening in body tissue. In an alternative embodiment, inner cannula 108 may be integrated into or replaced by an element of tube set 104. Inner cannula 108 may be comprised of any number of flexible or semi-rigid materials. For example, inner cannula 108 may be comprised of one or more polymers, elastomers, plastics, metals, composites, other similar materials, or combinations thereof.

Anchor assembly 110 is configured to locate a tissue opening, position closure system 100 relative to the tissue opening, and/or anchor the tissue surrounding the opening. Anchor assembly 110 includes an anchor portion 130 and an elongate portion 132. Anchor portion 130 is configured to be positioned and/or anchored against the distal surface of a tissue wall, such as an inside surface of a vessel wall. Elongate portion 132 is coupled to anchor portion 130 and is configured to control, deploy, position, stabilize, and/or retract anchor portion 130. In particular, elongate portion 132 may extend away from anchor portion 130 in a proximal direction through inner cannula 108, tube set 104, handle member 102, and/or plunger member 106. In one embodiment, elongate portion 132 is coupled at its proximal end 122 to plunger member 106. In one embodiment, elongate portion 132 is selectively detachable from plunger member 106 and recouplable thereto.

Anchor portion 130 may be disposed in an initial, contracted configuration within inner cannula 108. Elongate portion 132 extends proximally from anchor portion 130 to plunger member 106. In addition, elongate portion 132 may transfer forces from plunger member 106 to anchor portion 130. Accordingly, by advancing plunger member 106 or elongate portion 132 in a distal direction relative to inner cannula 108, an operator may deploy anchor portion 130 from the distal end of inner cannula 108. Retracting plunger member 106 in a proximal direction may position and/or anchor the anchor portion 130 against a distal surface of a tissue wall. In one embodiment, further retracting plunger member 106 in a proximal direction may retract anchor portion 130 from the tissue and/or into inner cannula 108 or tube set 104.

Anchor portion 130 is configured to move from an initial, contracted configuration within inner cannula 108 to a deployed, expanded configuration once deployed from inner cannula 108. To facilitate movement from the initial, contracted configuration to the deployed, expanded configuration, anchor portion 130 may be comprised of one or more superelastic or shape memory materials such as shape memory alloys. For example, and as will be explained in more detail below, anchor portion 130 may be heat set in the deployed, expanded configuration. Anchor portion 130 may then be elastically deformed into the initial, contracted configuration and disposed within inner cannula 108. In the initial, contracted configuration, anchor portion 130 may store sufficient energy to return to its deployed, expanded configuration once released from inner cannula 108.

In one embodiment, a user may operate plunger member 106 to deploy and/or retract anchor assembly 110. For example, plunger member 106 may be configured to at least partially receive tube set 104 and/or inner cannula 108. In one embodiment, plunger member 106 may also be configured to receive a portion of anchor assembly 110 and/or a guidewire. Inner cannula 108 and/or anchor assembly 110 may be coated, if desired, to minimize friction within inner cannula 108 to ease deployment.

A proximal end 134 of plunger member 106 may be configured to be gripped and/or operated by an operator, such as a physician. For example, an operator may grip handle member 102 with a first hand and grip proximal end 134 of plunger member 106 with a second hand in order to advance or retract plunger member 106 relative to handle member 102. In one embodiment, the operator may also rotate plunger member 106 relative to handle member 102, as discussed below. As a result, the operator may deploy anchor portion 130 of anchor assembly 110 from inner cannula 108 and/or position anchor portion 130 against a distal surface of a tissue wall thereby locating the tissue opening to be closed.

Thereafter, the operator may advance handle member 102 in a distal direction relative to plunger member 106 and inner cannula 108 to position distal end 124 of tube set 104 against a proximal surface of the tissue wall. By so doing, the operator may facilitate the closure of the tissue opening by at least partially gripping, sandwiching, and/or immobilizing the tissue surrounding the opening. The operator may then deploy a closure element into the tissue surrounding the opening to close the opening.

The shape of plunger member 106 may correspond with the shape of recess 118 of handle member 102 to facilitate relative movement between handle member 102 and plunger member 106. For example, the cross sectional shape of both plunger member 106 and recess 118 may be any shape desired such as circular, triangular, rectangular, or other shapes, or combinations thereof. In addition, the longitudinal length of plunger member 106 and the corresponding longitudinal depth of recess 118 may be any length and depth desired to allow sufficient relative movement between plunger member 106 and handle member 102. For example, the length of plunger member 106 and the corresponding depth of recess 118 may be sufficient to allow deployment of anchor portion 130 from inner cannula 108.

In one embodiment, closure system 100 includes a self-tensioning mechanism configured to automatically provide tension in anchor assembly 110 once anchor portion 130 has been deployed. For example, handle member 102 may include a spring mechanism disposed in recess 118 and configured to resist and/or counteract movement of plunger member 106 in a distal direction relative to handle member 102. In particular, advancing plunger member 106 in the distal direction relative to handle member 102 transfers energy to the spring mechanism, which is released once the operator releases plunger member 106.

As a result, the spring mechanism may move plunger member 106 in a proximal direction relative to handle member 102 thereby retracting anchor portion 130 in the proximal direction. As a result, anchor portion 130 may be caused to automatically engage the distal surface of the tissue wall. In addition, handle member 102 and tube set 104 may be caused to advance in a distal direction, thereby causing tube set 104 to engage the proximal surface of the tissue wall. The spring mechanism can also create sufficient tension within anchor assembly 110 to produce a desired pressure on the tissue between anchor portion 130 and tube set 104. Accordingly, because of the spring mechanism, closure system 100 may automatically and efficiently create the desired sandwiching or immobilizing force on the tissue surrounding the tissue opening. In addition, the spring mechanism may make it unnecessary for the operator to provide the movement or force necessary to position closure system 100 relative to the tissue opening. Other self-tensioning mechanisms may alternatively be included in closure system 100 to produce the desired tension in anchor assembly 110 and the required force upon the tissue surrounding the tissue opening. In one embodiment, plunger member 106 and closure system 100 have a click or ratchet function similar to that of a "click" pen.

If desired, closure system 100 may include a mechanism for determining the thickness of a tissue wall and/or the distance between anchor portion 130 and distal end 124 of tube set 104. For example, plunger member 106 may have a plurality of indicator lines (not shown) disposed along the length thereof. The indicator lines may be positioned and marked to indicate the position of the deployed anchor portion 130 relative to distal end 124 of tube set 104. In particular, the number of indicator lines exposed as plunger member 106 is retracted may indicate the thickness of the tissue surrounding the tissue opening being closed. The indicator lines may be calibrated so that an indication of zero thickness is obtained when anchor portion 130 is position directly against distal end 124 of tube set 104. As a result, the operator may refer to the indicator lines to determine the position of anchor portion 130 relative to distal end 124 of tube set 104 and/or the thickness of the tissue surrounding the opening.

Figure 2A:
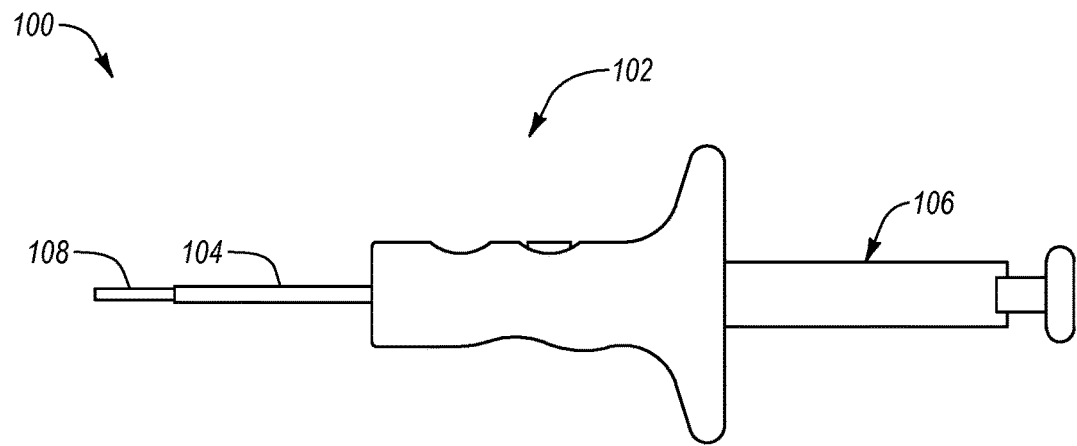
FIGS. 2A-2D illustrate one embodiment of a method of operating the closure system of FIG. 1.
Figure 2B:
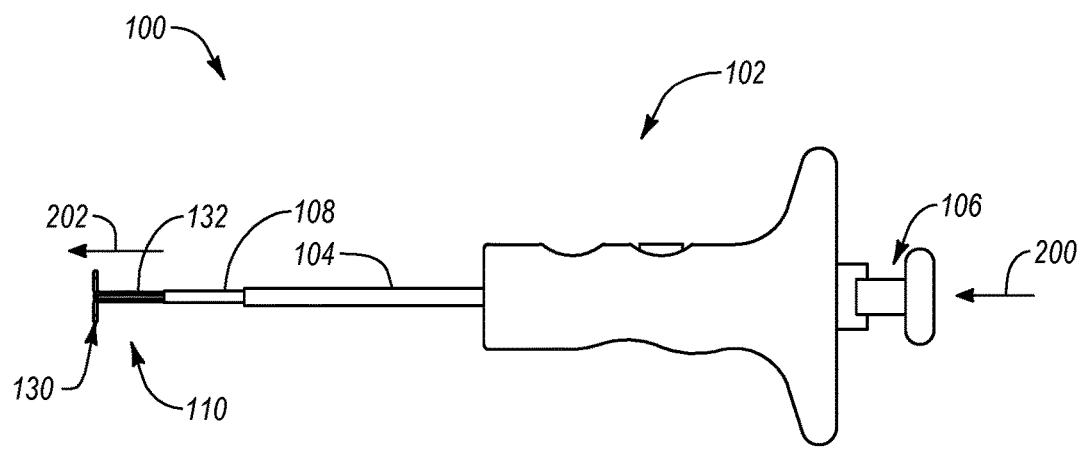

Reference is now made to FIGS. 2A-2D, which illustrate a method of operating closure system 100 of FIG. 1 according to one embodiment. FIG. 2A illustrates closure system 100 in an initial configuration. In this initial configuration, plunger member 106 is fully retracted proximally relative to handle member 102, and anchor portion 130 of anchor assembly 110 is disposed within inner cannula 108. As shown in FIG. 2B, plunger member 106 is advanced distally, as denoted by arrow 200, relative to handle member 102, tube set 104, and inner cannula 108. The distal advancement 200 of plunger member 106 causes anchor portion 130 of anchor assembly 110 to be deployed from distal end 126 of inner cannula 108, as denoted by arrow 202. As a result, anchor portion 130 moves from an initial, contracted configuration to a deployed, expanded configuration. In alternative embodiments, plunger member 106 may include two or more plunger components. For example, in one embodiment, plunger member 106 includes a first component configured to deploy and/or retract anchor assembly 110 and a second component configured to advance and/or retract inner cannula 108. In one embodiment, the first and second components of plunger member 106 are movable with respect to one another.

Figure 2C:
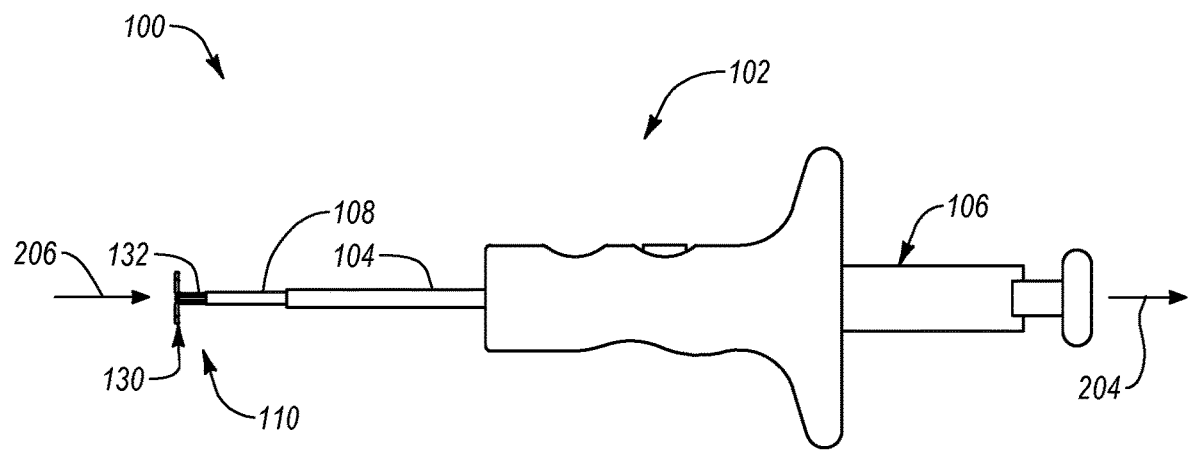
Figure 2D:
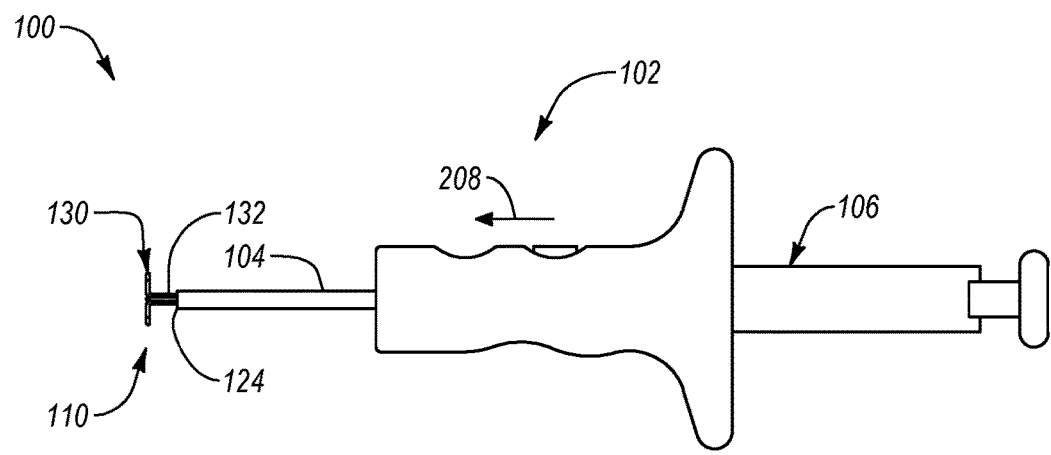

Once anchor portion 130 is in the deployed, expanded configuration, plunger member 106 is retracted proximally, denoted by arrow 204, relative to handle member 102, tube set 104, and/or inner cannula 108, as shown in FIG. 2C. The proximal retraction 204 of plunger member 106 also causes anchor portion 130 to be retracted, as denoted by arrow 206. As shown in FIG. 2D, handle member 102 is then advanced in the distal direction, denoted by arrow 208, relative to plunger member 106. The distal advancement 208 of handle member 102 advances tube set 104 in the distal direction until distal end 124 of tube set 104 is proximate anchor portion 130 of anchor assembly 110. As a result, an operator of closure system 100 may locate, anchor, and/or immobilize the tissue surrounding a tissue opening between tube set 104 and anchor portion 130. Thereafter, the operator may deploy a closure element into the tissue surrounding the tissue opening to close the opening.

Anchor assemblies may take many shapes and forms and may extend from the distal end of inner cannula 108 or from an opening on the wall thereof. Many various types of anchor assemblies that can be used in closure system 100 are disclosed in U.S. patent application Ser. No. 12/684,542, which was filed on Jan. 8, 2010, the disclosure of which is incorporated by reference in its entirety.

Figure 3A:
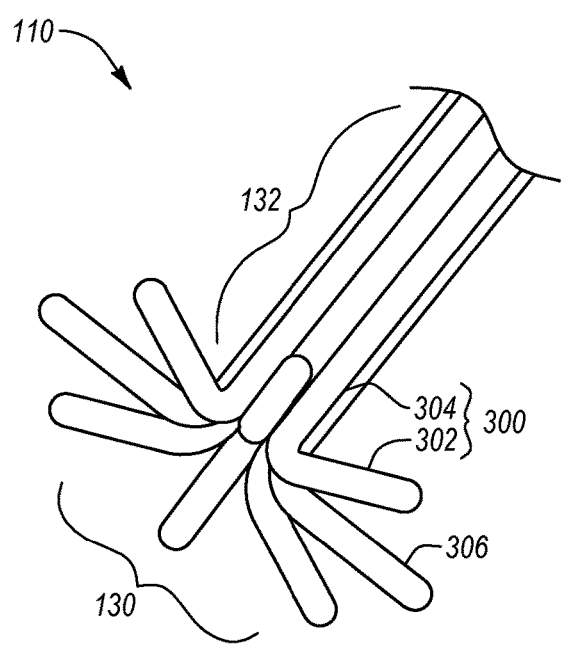
FIGS. 3A and 3B are perspective and end views, respectively, of an anchor assembly according to one embodiment.
Figure 3B:
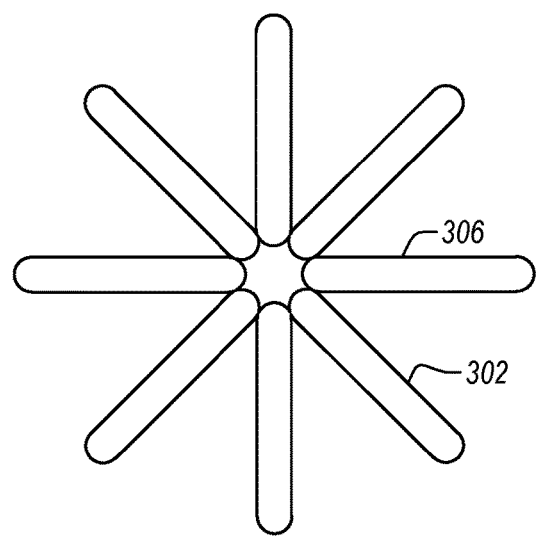

Turning to FIGS. 3A and 3B, anchor assembly 110 includes a plurality of anchor elements 300, each comprising an anchor portion 302 extending from an elongate portion 304. Anchor portions 302 of all anchor elements 300 combine to form anchor portion 130 of anchor assembly 110. Similarly, elongate portions 304 of all anchor elements 300 combine to form elongate portion 132 of anchor assembly 110. In the depicted embodiment, anchor assembly 110 has eight anchor elements 300. However, anchor assembly 110 may have fewer or more anchor elements 300, if desired.

Each anchor portion 302 comprises a projection 306 configured to engage the tissue surrounding an opening therein. Projection 306 may be shaped, positioned, and/or oriented in any configuration desired to provide positioning or anchoring support. For example, in the depicted embodiment, each projection 306 is substantially linear. In other embodiments, projections 306 can be curved, spiraled, multicurved, or any other shape. Furthermore, all or some of the anchor elements 300 can have similarly shaped projections or can comprise different shaped projections. In one embodiment, one or more projections 306 may extend in a direction or a plane substantially perpendicular to the longitudinal axis of elongate portion 132.

Each anchor portion 302 is coupled to the distal end of its corresponding elongate portion 304. In the depicted embodiment, anchor portion 302 and elongate portion 304 are generally orthogonal to each other to form an "L" shape, although this is not required. Furthermore, anchor elements 300 are positioned so that all of the elongate portions 304 are positioned adjacent each other and, as particularly shown in FIG. 3B, each projection 306 extends in a different radial direction away therefrom so as to not overlap. In one embodiment, one or more anchor portions 302 may overlap or cross over each other in order to increase resistance. Elongate portions 304 may be configured to advance, retract, position, and/or deploy anchor portions 302. In particular, elongate portions 304 may be longitudinally rigid or semi-rigid to facilitate advancing or retracting anchor portions 302. In one embodiment, elongate portions 304 may have a solid configuration such as a nitinol wire. In further embodiments, elongate portions 304 may have a generally tubular configuration.

Anchor portions 302 and/or elongate portions 304 may be comprised of any number of materials. In one embodiment, each anchor portion 302 may be comprised of the same materials as the corresponding elongate portion 304. In another embodiment, each anchor portion 302 may include different materials than the corresponding elongate portion 304. In one embodiment, all of the anchor portions 302 and/or elongate portions 304 are comprised of the same material.

Anchor elements 300 can be comprised of one or more elongated wires. For example, in the depicted embodiment, each corresponding anchor portion 302 and elongate portion 304 can comprise opposite ends of a single wire. In other embodiments, each corresponding anchor portion 302 and elongate portion 304 can comprise different wires that are attached or formed together. Any sized wire can be used so long as the anchor elements can extend through inner cannula 108. In some embodiments, the wires can vary in diameter between about 100 µm and about 300 µm, with between about 127 µm and about 178 µm being common. Other diameters are also possible. In addition, each wire can have a circular, oval, square, or other cross-sectional shape.

In one embodiment, each elongate portion 304 and corresponding anchor portion 302 may both be formed from a single shape memory or superelastic wire. The wire may be set into any shape desired for elongate portion 304 and anchor portion 302. For example, each wire may be set in an elongate form for elongate portion 304 and may be set with and elongate form or one or more bights or beds forming the expanded form of anchor portion 302. As shown in FIGS. 3A and 3B, in one configuration each wire may form projection 306.

Each anchor portion 302 may be configured to elastically deform to any shape and then return, once released, to its expanded shape. For example, each anchor portion 302 may be elastically deformed into an elongate and/or contracted configuration and disposed within lumen 111 of inner cannula 108 (See FIG. 4A). While in this contracted configuration, each anchor portion 302 may store sufficient energy to return to its expanded configuration. Once each anchor portion 302 is deployed from inner cannula 108, the anchor portion 302 may release the stored energy and return to its expanded configuration illustrated in FIGS. 3A and 3B.

In a further embodiment, one or more anchor portions 302 may include one or more gripping elements disposed along a proximal surface 308 thereof. The gripping elements may be configured to provide a frictional or immobilizing force on tissue surrounding a tissue opening. For example, one or more anchor portions 302 may include one or more ridges or teeth or barbs along proximal surfaces 308 that are configured to engage and grip or immobilize the tissue surrounding a tissue opening.

Reference is now made to FIGS. 4A-4D, which illustrate a method of deploying and retracting anchor assembly 110 from closure system 100 according to one embodiment.

Figure 4A:
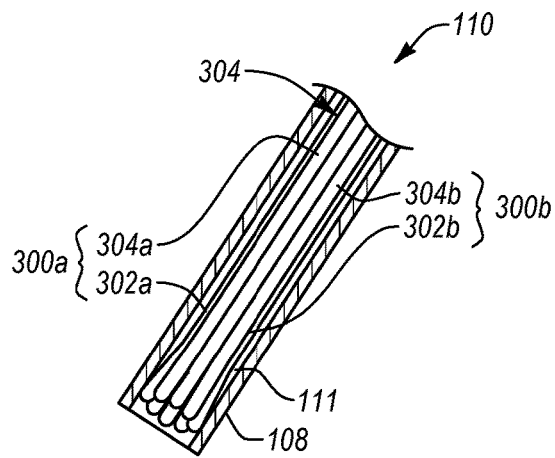
FIGS. 4A-4D illustrate one embodiment of a method of operating the anchor assembly of FIG. 3A using the closure system of FIG. 1.

FIG. 4A illustrates anchor assembly 110 disposed within lumen 111 of inner cannula 108 in an initial, contracted configuration. As discussed above, anchor assembly 110 includes a plurality of anchor elements 300 that each have an elongate portion 304 and an anchor portion 302. For example, anchor assembly 110 includes first and second anchor elements 300a and 300b that respectfully include first and second anchor portions 302a and 302b and first and second elongate portions 304a and 304b.

Figure 4B:
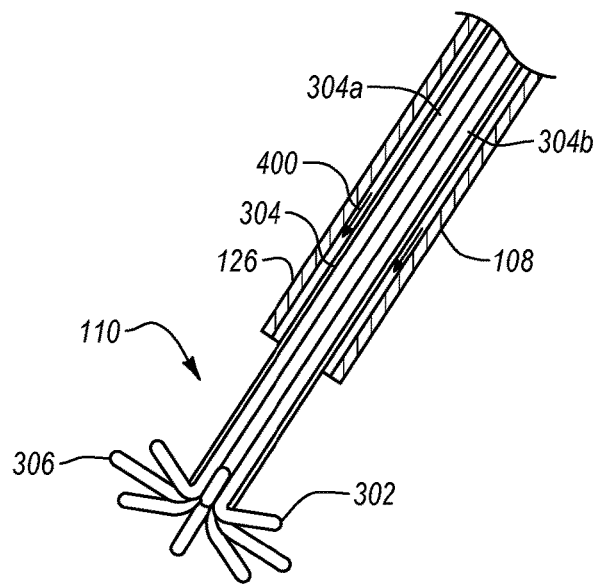

As shown in FIG. 4B, elongate portions 304 are advanced in a distal direction, denoted by arrows 400, relative to inner cannula 108. The distal advancement 400 of elongate portions 304 causes corresponding anchor portions 302 to deploy from distal end 126 of inner cannula 108. As a result, the distal advancement 400 of each elongate portion 304 causes each anchor portion 302 to move from the initial, contracted configuration shown in FIG. 4A to the deployed, expanded configuration shown in FIG. 4B. As discussed above, in the deployed, expanded configuration, each anchor portion 302 includes a projection 306 that radially extends away from the corresponding elongate portion 304.

Figure 4C:
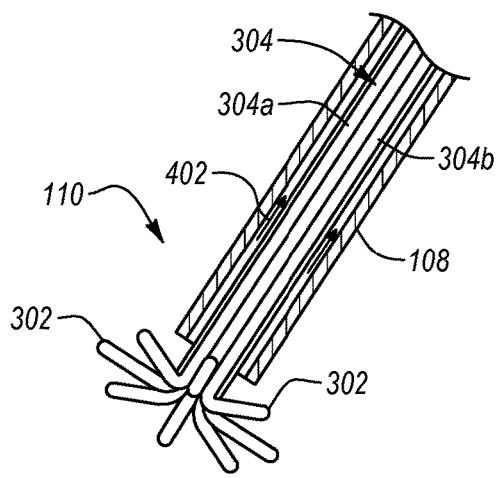

Once anchor portions 302 have been moved to the deployed, expanded configuration, elongate portions 304 can be retracted proximally, to provide an anchoring force, if needed. For example, as shown in FIG. 4C, retracting elongate portions 304 in the proximal direction, denoted by arrows 402, may cause anchor portions 302 to anchor against the distal surface of a tissue wall or any other surface against which anchor portions 302 are positioned.

Figure 4D:
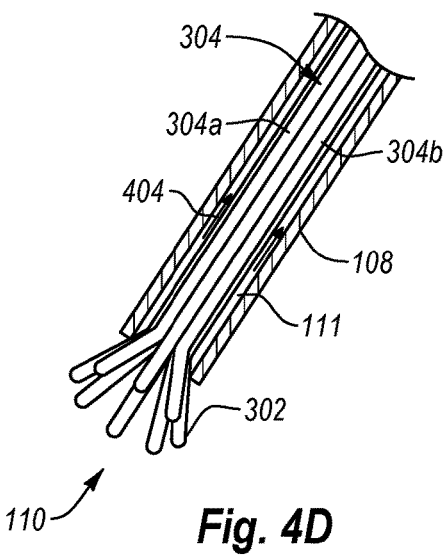

As shown in FIG. 4D, further retracting elongate portions 304 in the proximal direction, denoted by arrows 404, will cause each anchor portion 302 to retract back into lumen 111 of inner cannula 108 and move from the deployed, expanded configuration back to the contracted configuration.

Reference is now made to FIGS. 5A-5G, which illustrate a method of closing a tissue opening using closure system 100 according to one embodiment.

Figure 5A:
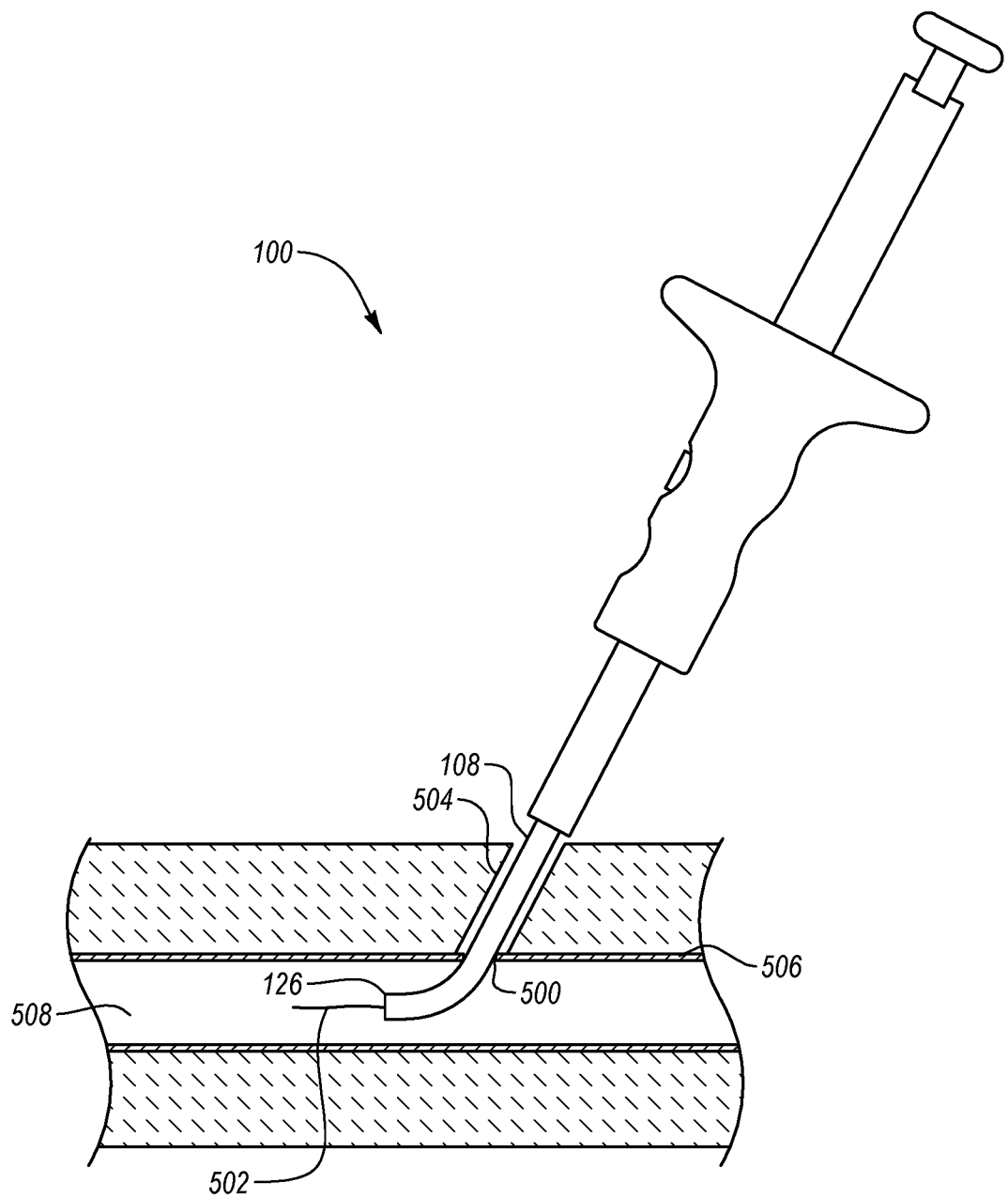
FIGS. 5A-5G illustrate one embodiment of a method of closing an opening in a body tissue using the anchor assembly of FIG. 3A and the closure system of FIG. 1.

As shown in FIG. 5A, closure system 100 may be at least partially advanced into a tissue opening 500. For example, after completing a percutaneous medical procedure, an operator may advance closure system 100 over a guidewire 502 through a tissue tract 504 and through tissue opening 500 in a tissue wall 506, such as a wall in a vein, artery, or other body vessel. In particular, the operator may advance closure system 100 until distal end 126 of inner cannula 108 extends through opening 500 into a vessel lumen 508. Once distal end 126 of inner cannula 108 has been advanced through opening 500, the operator may then retract guidewire 502 from vessel lumen 508.

Figure 5B:
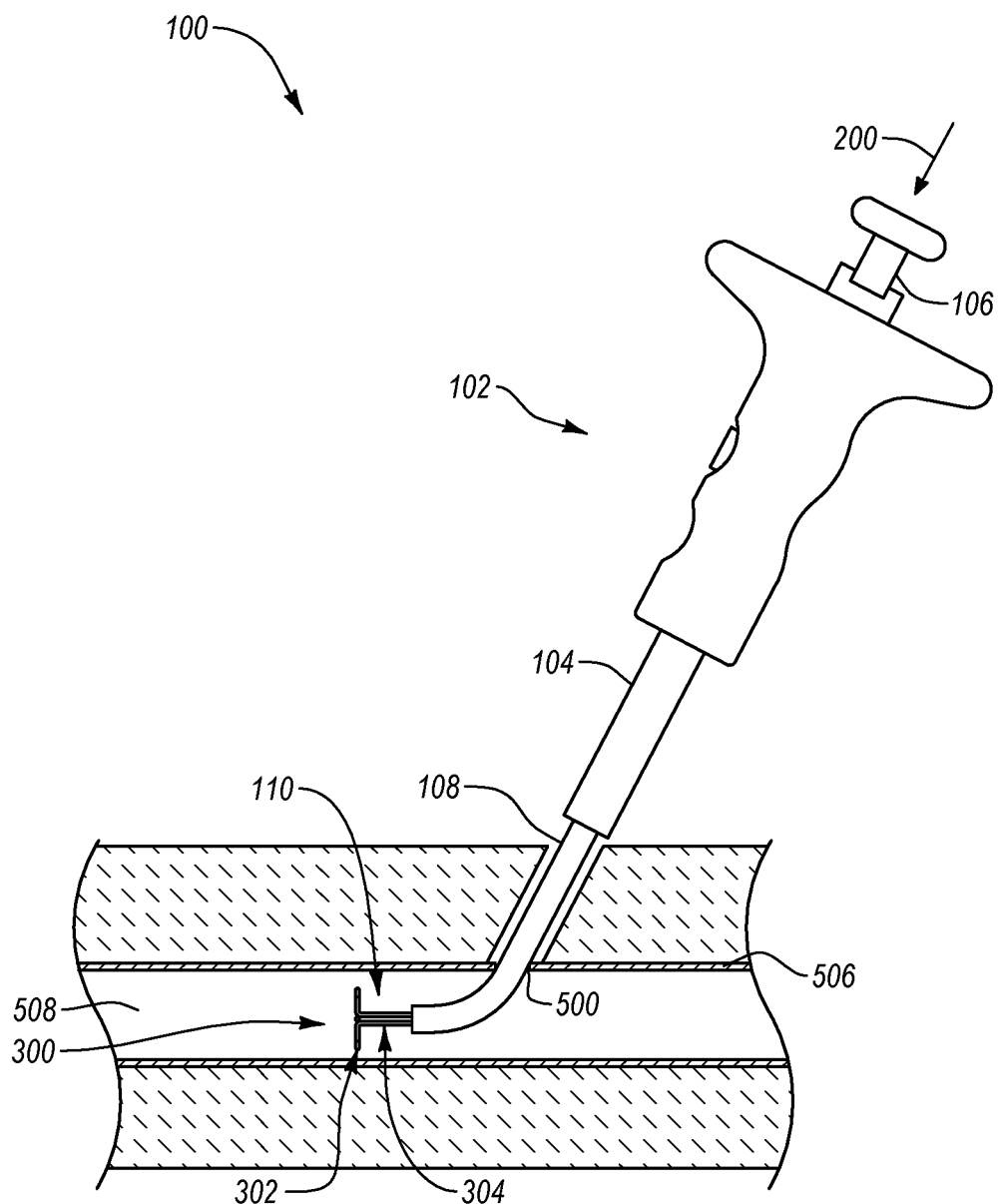

As shown in FIG. 5B, once closure system 100 has been advanced into vessel lumen 508, the operator may deploy anchor assembly 110 into body lumen 508. As explained in more detail above, the operator may deploy anchor assembly 110 by advancing plunger member 106 in a distal direction, denoted by arrow 200, relative to handle member 102, tube set 104, and inner cannula 108. Once deployed from inner cannula 108, each anchor portion 302 of anchor elements 300 of anchor assembly 110 moves from the initial, contracted configuration to the deployed, expanded configuration.

Figure 5C:
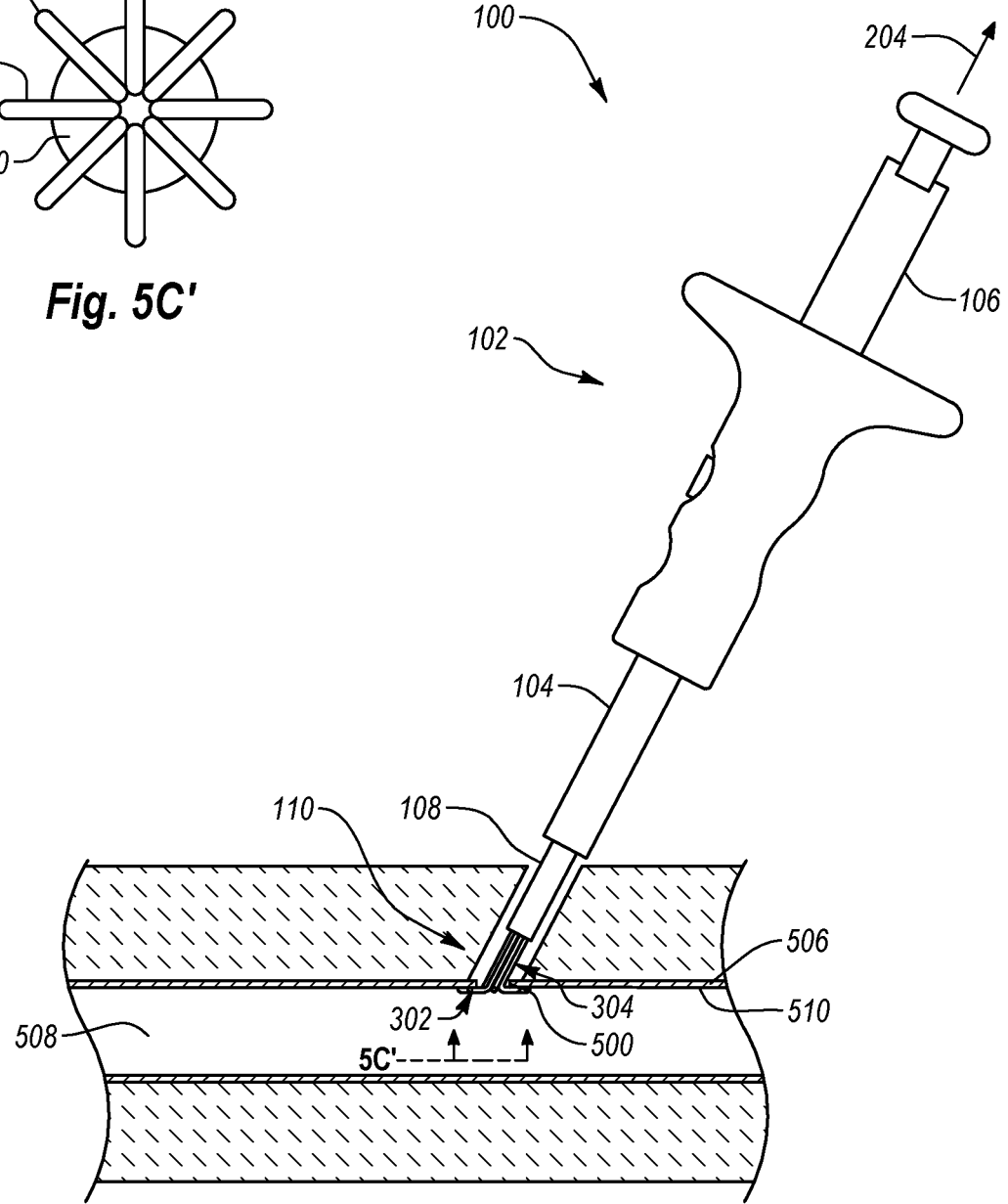
Figure 5C:
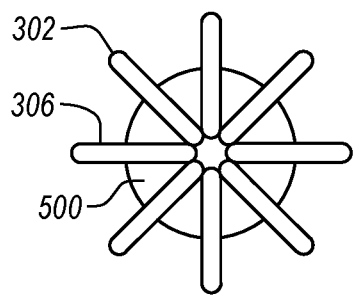

As shown in FIG. 5C, once anchor portions 302 of anchor elements 300 have been deployed within vessel lumen 508, the operator retracts plunger member 106 and/or closure system 100 proximally, as denoted by arrow 204, to position anchor portions 302 against the distal or inner surface 510 of tissue wall 506 proximate opening 500 as also shown in FIG. 5C'. In particular, the operator retracts plunger member 106 proximally until the operator feels the anchoring force or resistance from anchor portions 302 against distal surface 510 of tissue wall 506, thereby locating tissue opening 500 and anchoring or securing the tissue surrounding opening 500. As shown, the projections 306 of anchor portions 302 engage and anchor the tissue surrounding opening 500 in tissue wall 506. In particular, projections 306 each extend in a different radial direction that is substantially perpendicular to the longitudinal axis 120 of elongate portions 304, tube set 104, and/or inner cannula 108 to contact inner surface 510 of tissue wall 506 surrounding opening 500.

Figure 5D:
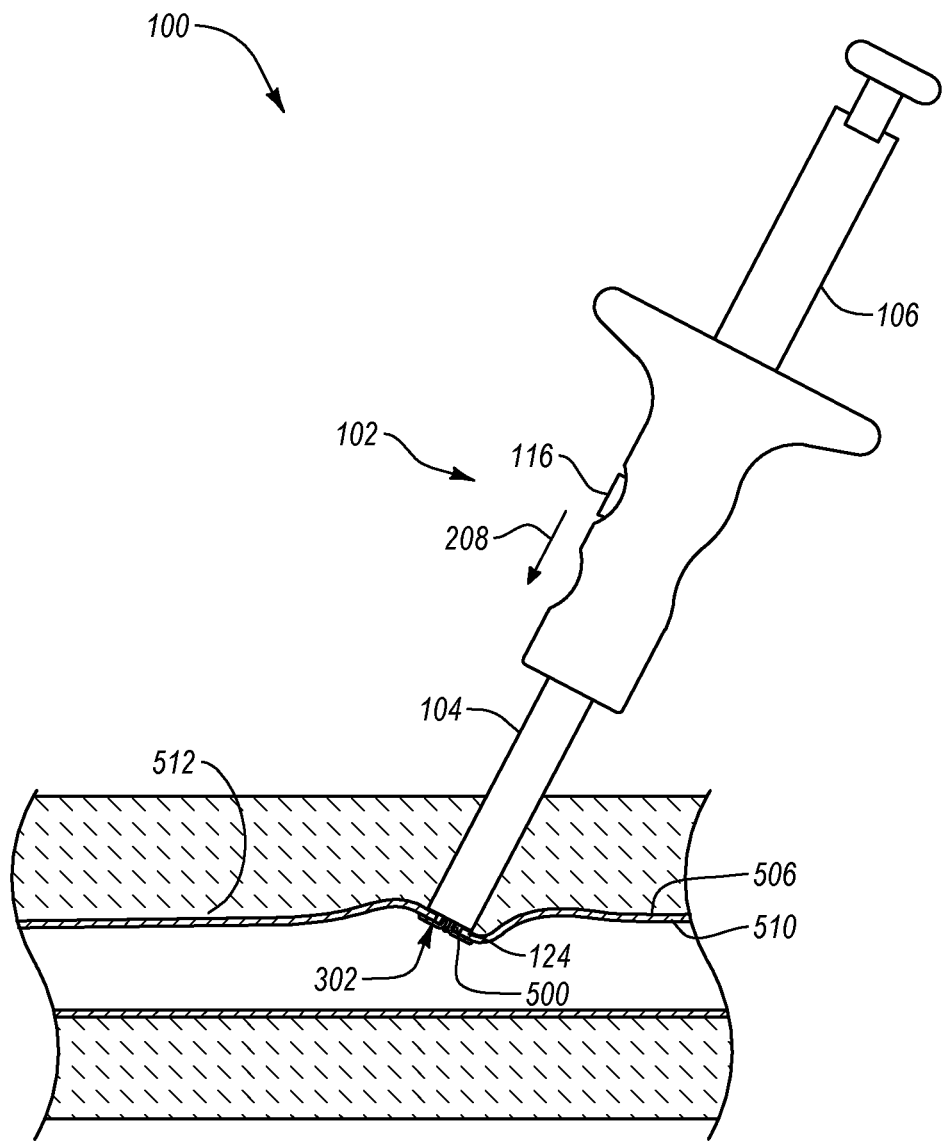

As shown in FIG. 5D, once anchor portions 302 have located tissue opening 500 and/or anchored or secured the tissue surrounding opening 500, the operator advances handle member 102 distally, denoted by arrow 208, relative to plunger member 106 to advance tube set 104 in the distal direction relative to anchor portions 302. In particular, the operator advances handle member 102 and/or tube set 104 until distal end 124 of tube set 104 engages the proximal or outer surface 512 of tissue wall 506 proximate or surrounding tissue opening 500. As a result, in one embodiment, by advancing tube set 104 in the distal direction and/or retracting anchor portions 302 in the proximal direction, the operator may sandwich the tissue surrounding tissue opening 500 between tube set 104 and anchor portions 302. Accordingly, the operator thereby engages and/or at least partially immobilizes the tissue surrounding opening 500.

Figure 5E:
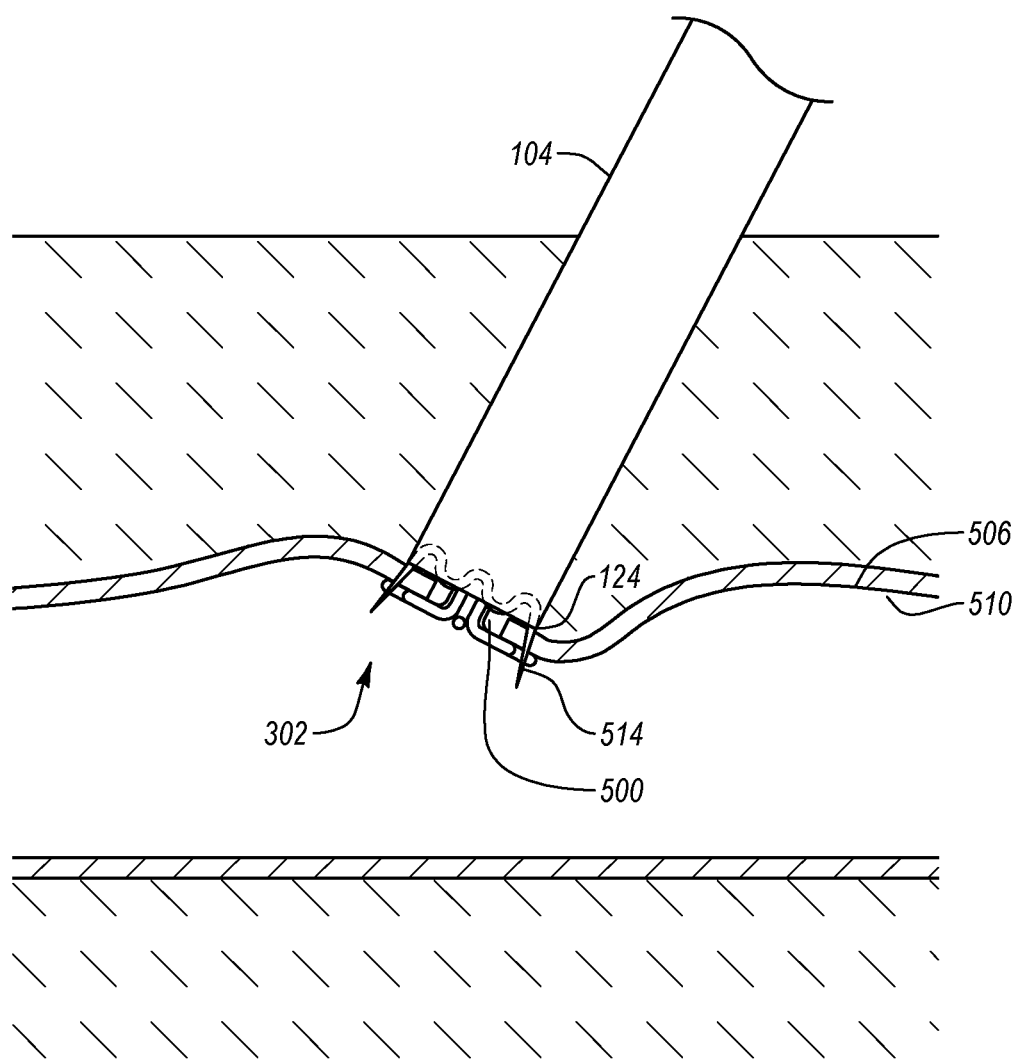

If desired, a closure element can then be deployed into the tissue surrounding opening 500 to facilitate the closure of tissue opening 500. Tube set 104 and anchor portions 302 may hold the tissue in place while a closure element is deployed into the tissue. For example, as shown in FIG. 5E, once tube set 104 and anchor portions 302 are sandwiching tissue wall 506, the operator may deploy a closure element 514 into the tissue surrounding tissue opening 500. In one embodiment, the operator may depress button 116 (FIG. 5D) to eject or deploy closure element 514 into tissue wall 506. In particular, closure element 514 may be deployed from an initial, open configuration to a deployed, closed configuration, thereby engaging and bringing the tissue surrounding tissue opening 500 together to close opening 500. Closure element 514 may include any device configured to close tissue opening 500. For example, closure element 514 may comprise a staple, a clip, other similar devices, or combinations thereof.

Figure 5F:
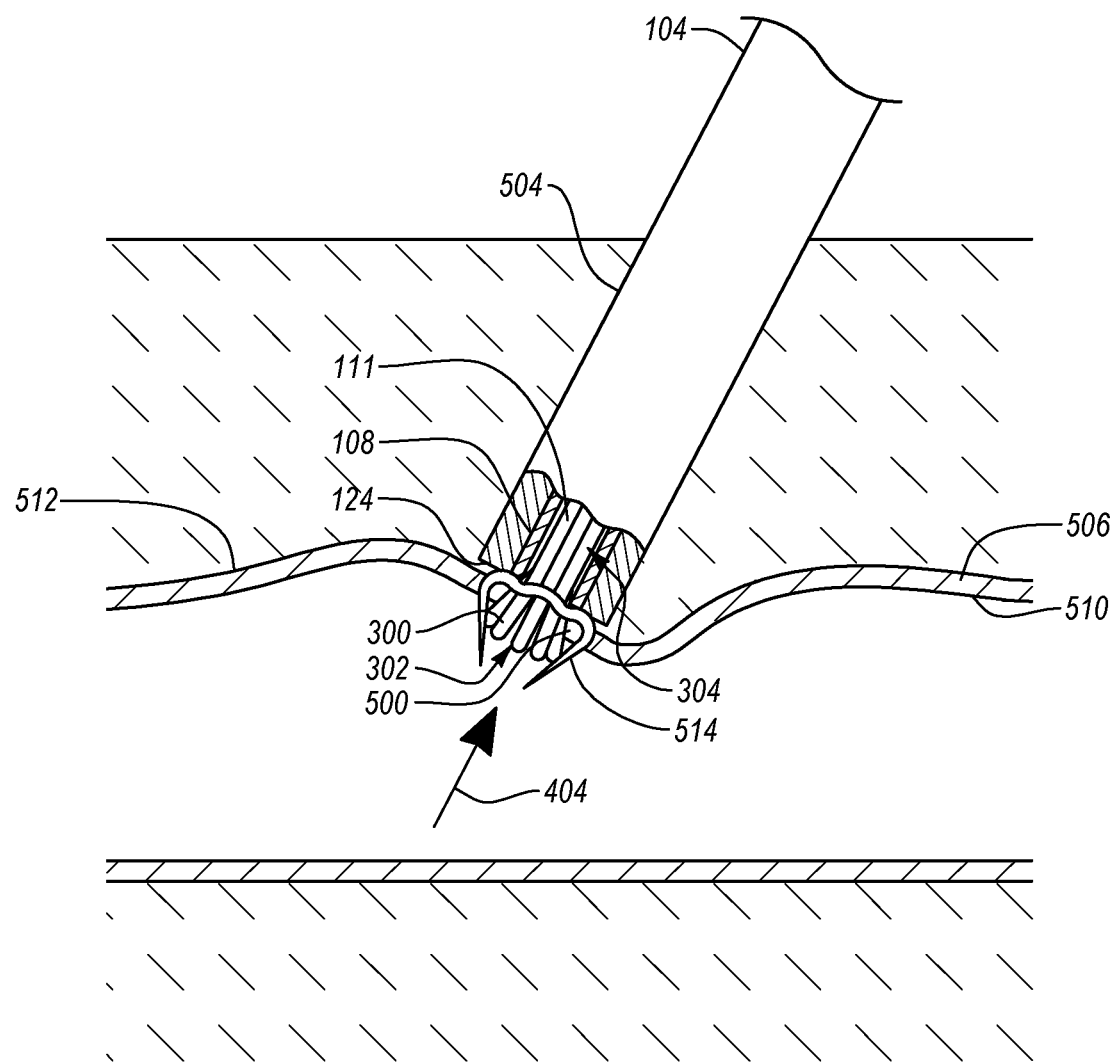

Thereafter, as shown in FIG. 5F, anchor elements 300 may be retracted by moving elongate portions 304 in the proximal direction, as denoted by arrow 404.

As shown in the depicted embodiment, inner cannula 108 can be held in place against outer surface 512 of tissue wall 506 and/or abutting closure element 514 while anchor assembly 110 is retracted. Holding inner cannula 108 against proximal wall 506 and/or abutting closure element 514 may provide sufficient force to allow anchor assembly 110 and more particularly anchor portions 302 to deform into the pre-deployment state inside lumen 111 of inner cannula 108. This ensures that the closure element 514 does not become dislodged as anchor portions 302 are withdrawn and contracted.

As also shown in the depicted embodiment, distal end 124 of tube set 104 can also remain engaged with outer surface 512 of tissue wall 506 and/or abutting closure element 514 during the retraction of anchor elements 300. As a result, the tissue can be supported by tube set 104 and therefore is less likely to be torn, abraded, or otherwise further damaged by anchor elements 300 as the anchors are retracted. In this manner, anchor assembly 110 can atraumatically collapse and be withdrawn from the tissue without causing significant damage to tissue wall 506.

Alternatively, anchor elements 300 may be retracted after handle member 102 (FIG. 5D), tube set 104, and/or inner cannula 108 are retracted out of and/or away from tissue wall 506 and tissue tract 504.

In one embodiment anchor portions 302 are pulled through closure element 514 after closure element 514 has been deployed and contracted. Closure elements 514 may have superelastic properties to facilitate the withdrawal of anchor portions 302 through closure element 514. For example, closure element 514 may at least partially expand to facilitate the withdrawal of anchor portions 302 and then return to a contracted position to close tissue opening 500. In another embodiment, anchor portions 302 and closure element 514 are positioned so that anchor portions are not pulled through closure element 514 when anchor portions 302 are retracted.

The shape and size of anchor elements 300 with respect to closure element 514 can aid in allowing anchor elements 300 to be retracted after closure element 514 has been deployed. For example, the wires used to form anchor elements 300 can be substantially smaller than closure element 514. As a result, pulling anchor portions 302 through closure element 514 may not affect the positioning of closure element 514 since closure element 514 anchors into the tissue by design. In some embodiments, the wires used to form anchor elements 300 can radially move inward towards each other (i.e., radially compress) during retraction to together form a small cross sectional area. This can help in allowing closure element 514 to be deployed and positioned without interfering therewith. In one embodiment, the wires of anchor portions 302 are superelastic with a diameter small enough to not require substantial force to collapse anchor portions 302 and pull them through the deployed closure element 514. For example, the anchor wires may each have a diameter of around 0.005-0.007" (127 μm-178 μm).

Furthermore, by being comprised of separate thin wires, each anchor element 300 can pass by closure element 514 during retraction without snagging or otherwise catching on closure element 514. Furthermore, because anchor elements 300 are each comprised of a separate wire that has only a single end protruding therefrom, there is less chance that snagging or other type of hold up will occur even if there is contact with closure element 514. These anchor element attributes also ensure that closure element 514 does not become dislodged as anchor elements 300 are withdrawn and contracted. In light of the above, anchor assembly 110 can atraumatically collapse and be withdrawn through closure element 514 without causing significant damage to tissue wall 506.

Figure 5G:
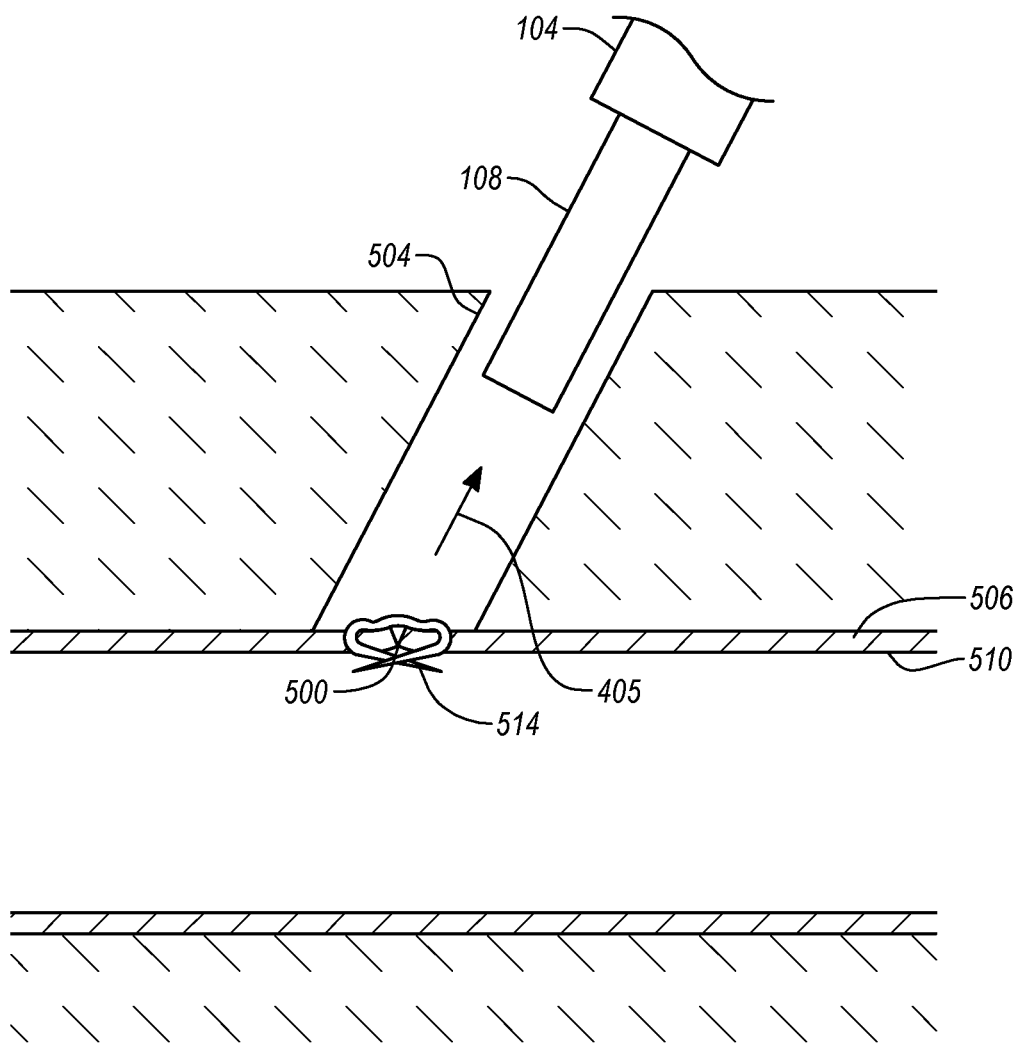

As shown in FIG. 5G, once closure element 514 has been deployed and anchor elements 300 have been retracted, handle member 102 (FIG. 5D), tube set 104, and inner cannula 108 may be retracted proximally out of and/or away from tissue wall 506 and tissue tract 504, as denoted by arrow 405.

Accordingly, by following one or more of the acts disclosed in FIGS. 5A-5G, an operator may efficiently close tissue opening 500 with a greater amount of flexibility and control. And as noted above, the anchor assembly can atraumatically collapse and be withdrawn from the tissue without causing significant damage to the tissue wall.

The anchor assemblies of the closure systems disclosed herein can be made of a single material or of multiple materials. This can include a metal primary material and polymer/drug topcoat or a different metal top layer. The multiple layers can be made of resiliently flexible materials or rigid and inflexible materials, and selected combinations thereof. The use of resiliently flexible materials can provide force-absorbing characteristics, which can also be beneficial for absorbing stresses and strains, which may inhibit crack formation at high stress zones. Also, the multiple layers can be useful for applying radiopaque materials.

Embodiments of the anchor assemblies can be comprised of a material made from any of a variety of known suitable biocompatible materials, such as a biocompatible shape memory material (SMM). SMMs have a shape memory effect in which they can be made to remember a particular shape. Once a shape has been remembered, the SMM may be bent out of shape or deformed and then returned to its original shape by unloading from strain or heating. Typically, the SMMs can be shape memory alloys (SMA) comprised of metal alloys, or shape memory plastics (SMP) comprised of polymers. The materials can also be referred to as being superelastic.

Some examples of SMAs that can be used with the embodiments of the present application include, but are not limited to: copper-zinc-aluminum; copper-aluminum-nickel; nickel-titanium (NiTi) alloys known as nitinol; nickel-titanium platinum; nickel-titanium palladium; and cobalt-chromium-nickel alloys or cobalt-chromium-nickel-molybdenum alloys known as elgiloy alloys.

It can be beneficial to include at least one layer of an SMA and at least one layer of an SMP to form a multilayered body; however, any appropriate combination of materials can be used to form a multilayered device. Examples of SMPs that can be used in embodiments of the present application include, but are not limited to, biodegradable polymers, such as oligo(ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined. As such, any SMP can be used in accordance with the present disclosure.

Also, the anchor assemblies can be comprised of a variety of known suitable deformable materials, including, but not limited to, stainless steel, silver, platinum, tantalum, palladium, nickel, titanium, nitinol, nitinol having tertiary materials (see U.S. Patent Application Publication No. 2005/0038500, which is incorporated herein by reference, in its entirety), niobium-tantalum alloy optionally doped with a tertiary material (see U.S. Patent Application Publications No. 2004/0158309, 2007/0276488, and 2008/0312740, which are each incorporated herein by reference, in their entireties) cobalt-chromium alloys, or other known biocompatible materials. Such biocompatible materials can include a suitable biocompatible polymer in addition to or in place of a suitable metal. The polymeric closure element can include biodegradable or bioabsorbable materials, which can be either plastically deformable or capable of being set in the deployed configuration.

In one embodiment, the anchor assemblies can be made at least in part of a high strength, low modulus metal alloy comprising Niobium, Tantalum, and at least one element selected from the group consisting of Zirconium, Tungsten, and Molybdenum.

In further embodiments, the anchor assemblies can be made from or be coated with a biocompatible polymer. Examples of such biocompatible polymeric materials can include hydrophilic polymer, hydrophobic polymer biodegradable polymers, bioabsorbable polymers, and monomers thereof. Examples of such polymers can include nylons, poly(alpha-hydroxy esters), polylactic acids, polylactides, poly-L-lactide, poly-DL-lactide, poly-L-lactide-co-DL-lactide, polyglycolic acids, polyglycolide, polylactic-co-glycolic acids, polyglycolide-co-lactide, polyglycolide-co-DL-lactide, polyglycolide-co-L-lactide, polyanhydrides, polyanhydride-co-imides, polyesters, polyorthoesters, polycaprolactones, polyesters, polyanydrides, polyphosphazenes, polyester amides, polyester urethanes, polycarbonates, polytrimethylene carbonates, polyglycolide-co-trimethylene carbonates, poly(PBA-carbonates), polyfumarates, polypropylene fumarate, poly(p-dioxanone), polyhydroxyalkanoates, polyamino acids, poly-L-tyrosines, poly(beta-hydroxybutyrate), polyhydroxybutyrate-hydroxyvaleric acids, polyethylenes, polypropylenes, polyaliphatics, polyvinylalcohols, polyvinylacetates, hydrophobic/hydrophilic copolymers, alkylvinylalcohol copolymers, ethylenevinylalcohol copolymers (EVAL), propylenevinylalcohol copolymers, polyvinylpyrrolidone (PVP), combinations thereof, polymers having monomers thereof, or the like.

Figure 6A:
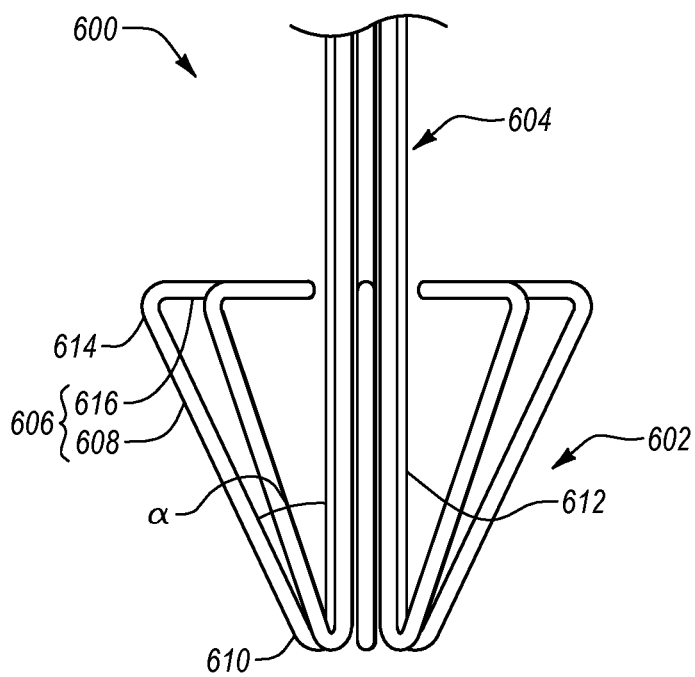
FIG. 6A is a side view of another embodiment of an anchor assembly in the deployed position.

Reference is now made to FIGS. 6A-6D, which illustrate an anchor assembly 600 according to another embodiment. As shown in FIG. 6A, anchor assembly 600 is similar to anchor assembly 110 in that it too includes a plurality of anchor elements 601 each having an elongate portion 604 and an anchor portion 602 radially extending therefrom. However, instead of having projections 306 that are substantially straight and orthogonal to the longitudinal axis of closure system 100 in the deployed position, each anchor portion 602 comprises a projection 606 that in its deployed, expanded state folds back proximally with respect to anchor portion 602. Specifically, each projection 606 includes a first section 608 having a first end 610 coupled to the distal end 612 of elongate portion 604. First section 608 extends proximally from first end 610 to a spaced apart second end 614. First section 608 forms an angle α with respect to elongate portion 604. Angle α can be any desired acute angle. For example, in one embodiment, angle α is in a range between about 10 degrees and about 75 degrees with between about 15 degrees and about 45 degrees being more common. Other angle values can also be used.

Each projection 606 can also include one or more further sections, if desired. For example, in the depicted embodiment, each projection 606 includes a second section 616. Second section 616 extends from second end 614 of first section 608 at least partially toward the corresponding elongate portion 604. Second section 616 can alternatively extend in other directions, if desired. In the depicted embodiment, second section 616 is substantially orthogonal to elongate portion 604 in the deployed configuration, although this is not required.

Similar to the previous embodiments, anchor elements 601 may be comprised of one or more shape memory materials and may be heat set to have a memory shape. For example, anchor elements 601 may be heat set when their corresponding projections 606 are in the expanded configuration shown in FIG. 6A. As a result, when anchor portion 602 is deployed, each projection 606 may superelastically move to its expanded configuration. Thereafter, a user may apply a force to anchor portion 602 to deform each projection 606 away from its memory shape and contract anchor portion 602. Alternatively, each projection 606 may have a contracted memory shape and the user may apply a force to anchor portion 602 to move anchor portion 602 to an expanded configuration.

Figure 6B:
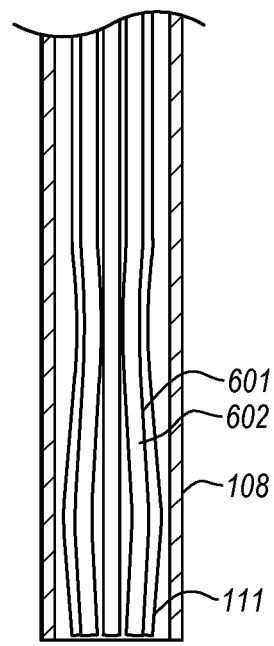
FIG. 6B is a cross sectional side view of the anchor assembly of FIG. 6A in the retracted position.
Figure 6C:
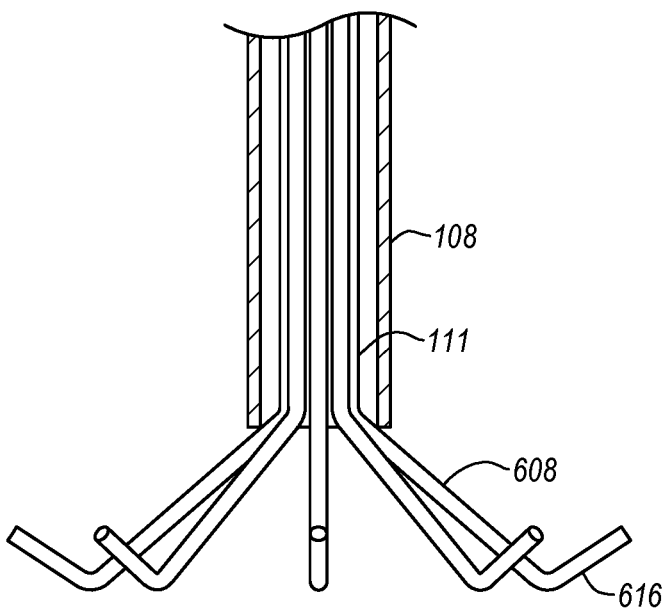
FIGS. 6C and 6D are cross sectional side views of the anchor assembly of FIG. 6A depicting the anchor assembly as it is moved from the deployed to the retracted position.
Figure 6D:
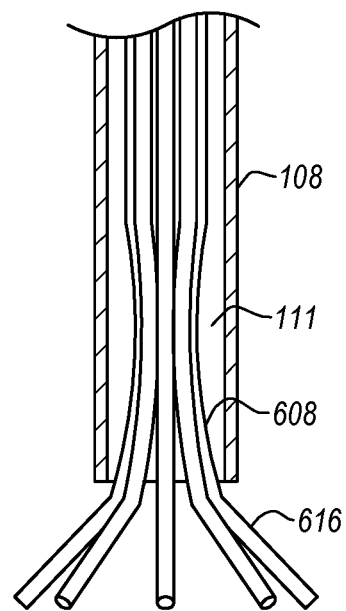

During use, anchor elements 601 perform similar to anchor elements 300. That is, as shown in FIG. 6B, while anchor elements 601 are positioned within lumen 111 of inner cannula 108, anchor portions 602 are in a similar initial contracted configuration. Once anchor elements 601 are deployed, anchor portions 602 move to the deployed, expanded configuration shown in FIG. 6A. Finally, when retracted back into lumen 111, anchor portions 602 again move to the contracted configuration. The movement to the contracted configuration may occur in steps, corresponding to when each section retracts into lumen 111. For example, for each anchor portion 602, first section 608 will first begin to move to the contracted configuration as first section 608 moves into lumen 111, as shown in FIG. 6C. As anchor portion 602 continues to be retracted, first section 608 will continue to be contracted and second section 616 will begin to move to the contracted configuration as second section 616 moves into lumen 111, as shown in FIGS. 6D and 6D.

Similar to anchor elements 300, in some embodiments anchor elements 601 can also radially compress during retraction to allow closure element 514 to be deployed and positioned without interference therefrom.

Figure 7:
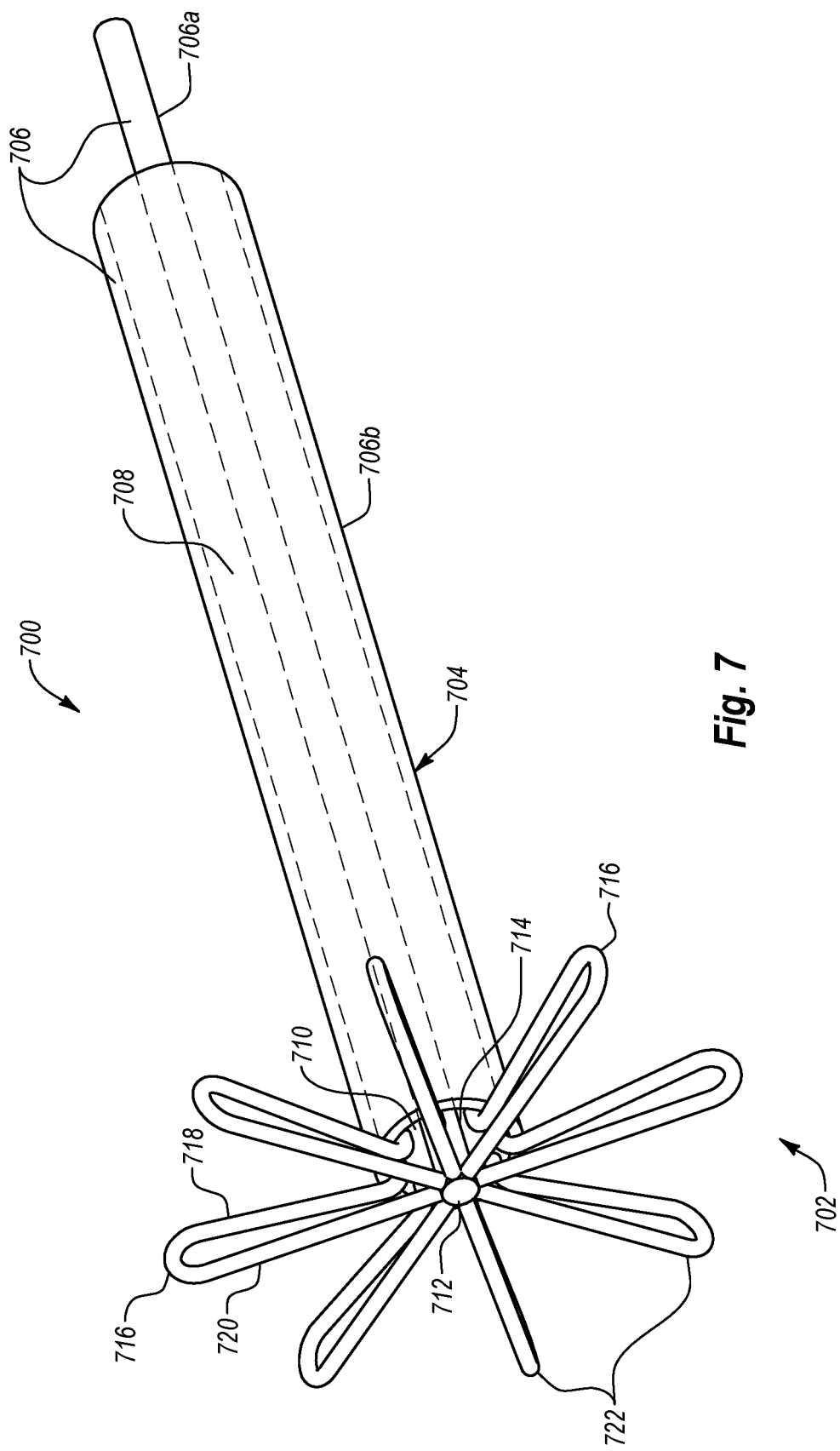
FIG. 7 is a perspective view of another embodiment of an anchor assembly in the deployed position.

Reference is now made to FIG. 7, which illustrates a perspective view of an anchor assembly 700 according to another embodiment. Similar to previously discussed anchor assemblies, anchor assembly 700 includes an anchor portion 702 and an elongate portion 704. Elongate portion 704 may include a plurality of elongate members 706. For example, in the depicted embodiment, elongate portion 704 includes a first elongate member 706a extending through a lumen 708 of a second elongate member 706b. In alternative embodiments, first elongate member 706a may instead be positioned to the side of second elongate member 706b. First elongate member 706a may comprise a mandrel or a push/pull wire or the like that extends to a distal end 710. First elongate member 706a may also include a cap 712 coupled to the mandrel or wire at distal end 710. First elongate member 706a may include one or more shape memory materials, such as nitinol, spring steel, and/or other shape memory alloys, although this is not required. Alternatively, first elongate member 706a may include one or more other metals or polymers.

Second elongate member 706b extends to a distal end 714 and may be generally tubular in shape. In one embodiment, second elongate member 706b serves as a guidewire, providing flexibility for easy access and navigation throughout a medical procedure. In one embodiment, second elongate member 706b is configured to house anchor portion 702 therein in an undeployed, contracted configuration until a user desires to deploy anchor portion 702 to locate or anchor the tissue surrounding a tissue opening, as described in more detail below. Second elongate member 706b may be comprised of the same types of materials discussed above regarding first elongate member 706a. Although depicted as a solid tube, second elongate member 706b may alternatively comprise a braided wire tube, a coiled wire, or other similar structures.

Anchor portion 702 can include a plurality of wires or the like that may extend between the distal ends of elongate members 706. For example, in the depicted embodiment, anchor portion 702 comprises a plurality of wires 716 that each extend from a proximal end 718 connected to distal end 714 of second elongate member 706b to a distal end 720 connected to distal end 714 of elongate member 706a. If a cap 712 is used, distal ends 720 of wires 716 can alternatively connect thereto. The connections between wires 716 and first and second elongate members 706a and 706b can be achieved through welding, adhesives, or any other known fastening mechanism. Alternatively, wires 716 can be integrally formed with first elongate member 706a and/or second elongate member 706b.

Each wire 716 can include a projection 722 extending away from the longitudinal axis of elongate portion 704. Projections 722 are configured to have a deployed, expanded configuration, as shown in FIG. 7, an undeployed contracted configuration, and a deployed, contracted configuration, as discussed in greater detail below. In the deployed, expanded configuration, each projection 722 has a loop-like shape. In other embodiments, each projection 722 may have any shape or size desired for a particular application. In addition, anchor portion 702 may comprise any number of wires 716 desired. For example, although FIG. 7 illustrates anchor portion 702 as having eight wires 716 and eight corresponding projections 722, any number of wires 716 and projections 722 can be used. For example, anchor portion 702 can alternatively comprise less than or more than eight wires 716 and projections 722.

Similar to the previous embodiments, wires 716 may be comprised of one or more shape memory materials and may be heat set to have a memory shape. For example, wires 716 may be heat set when their corresponding projections 722 are in the expanded configuration shown in FIG. 7. As a result, when anchor portion 702 is deployed, each projection 722 may superelastically move to its expanded configuration. Thereafter, a user may apply a force to anchor portion 702 to deform each projection 722 away from its memory shape and contract anchor portion 702. Alternatively, the each projection 722 may have a contracted memory shape and the user may apply a force to anchor portion 702 to move anchor portion 702 to an expanded configuration.

Figure 8A:
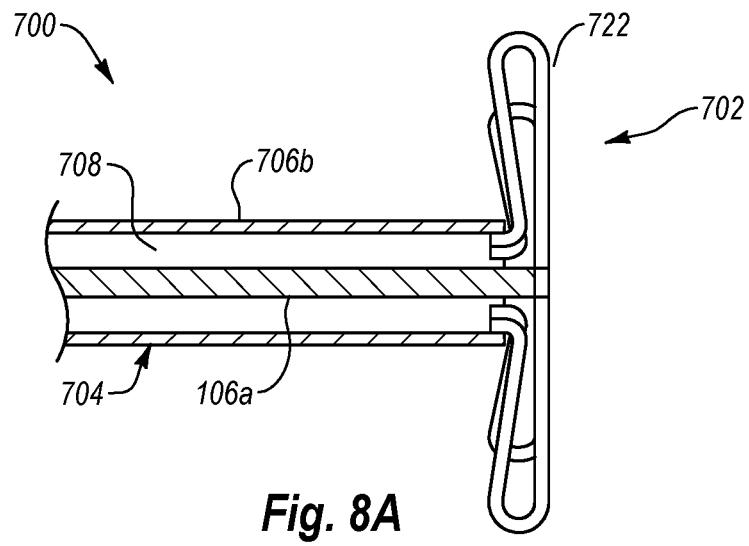
FIGS. 8A-8C are cross sectional side views of the anchor assembly of FIG. 7 in a deployed/expanded configuration, a retracted/collapsed configuration, and a deployed/collapsed configuration, respectively.
Figure 8B:
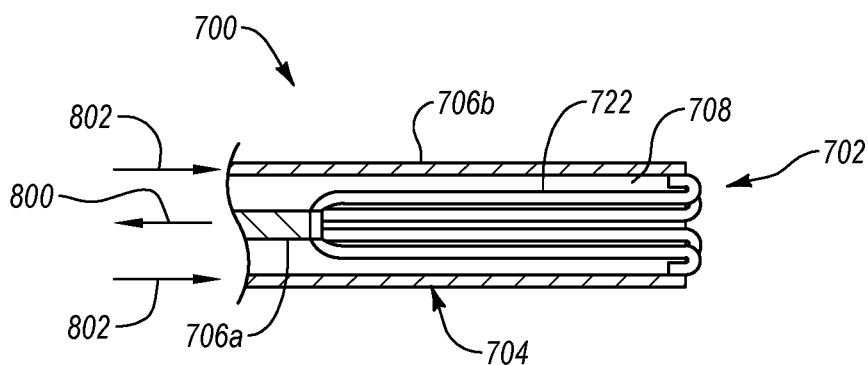
Figure 8C:
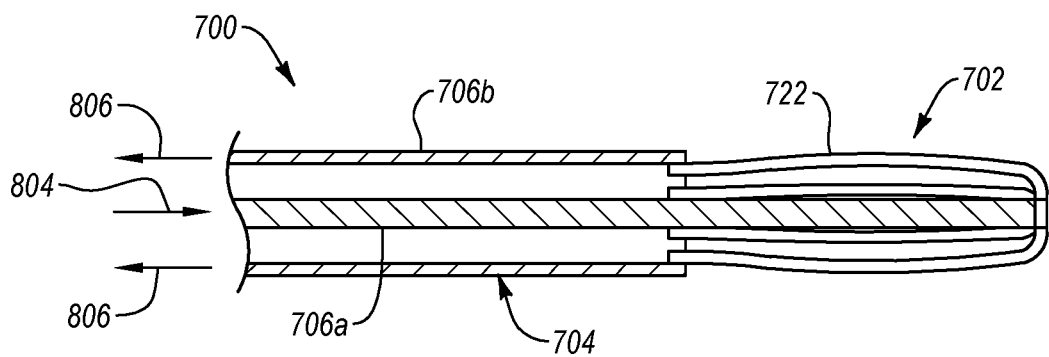

Reference is now made to FIGS. 8A-8C, which side views of anchor assembly 700 of FIG. 7 in various configurations. Specifically, FIG. 8A illustrates anchor assembly 700 with anchor portion 702 in the deployed expanded configuration, FIG. 8B illustrates anchor assembly 700 in the undeployed contracted configuration, and FIG. 8C illustrates anchor assembly 700 in the deployed contracted configuration.

As shown in FIG. 8A, anchor portion 702 of anchor assembly 700 has an expanded configuration in which projections 722 extend substantially perpendicularly away from the longitudinal axis of elongate members 706. In one embodiment, the expanded configuration of anchor portion 702 may be formed when elongate projections 722 fold roughly upon themselves with the bend of each projection 722 extending radially outward.

As shown in FIGS. 8B and 8C, anchor portion 702 may have a variety of contracted configurations. For example, in the undeployed contracted configuration of FIG. 8B, projections 722 are retracted into lumen 708 of second elongate member 706b. This can be done by moving first elongate member 706a in a proximal direction, denoted by arrow 800, relative to second elongate member 706b, or moving second elongate member 706b in a distal direction, denoted by arrows 802, relative to first elongate member 706a, or any combination thereof. Having anchor portion 702 in the undeployed contracted configuration shown in FIG. 8B may facilitate the delivery of anchor assembly 700 into a tissue opening or the retraction of anchor assembly 700 from a tissue opening.

For example, a user may maintain tension 800 in first elongate member 706a as anchor assembly 700 is advanced at least partially through the tissue opening. Thereafter, the user may release the tension on first elongate member 706a, after which anchor portion 702 may move superelastically to the expanded configuration shown in FIG. 8A. Alternatively, the user may facilitate deployment of anchor portion 702 by advancing first elongate member 706a distally with respect to second elongate member 706b.

In the deployed contracted configuration shown in FIG. 8C, projections 722 are elongated and drawn radially inwardly by moving first elongate member 706a in the distal direction, denoted by arrow 804 relative to second elongate member 706b, or moving second elongate member 706b in a proximal direction, denoted by arrows 806, relative to first elongate member 706a, or any combination thereof. Similar to the undeployed contracted configuration, having anchor portion 702 in the deployed contracted configuration shown in FIG. 8C may facilitate the delivery of anchor assembly 700 into a tissue opening or the retraction of anchor assembly 700 from a tissue opening. For example, a user may maintain the distal force 804 in first elongate member 706a as anchor assembly 700 is advanced at least partially through the tissue opening. Thereafter, the user may release the force on first elongate member 706a, after which anchor portion 702 may move superelastically to the expanded configuration shown in FIG. 8A. Alternatively, the user may facilitate deployment of anchor portion 702 by advancing second elongate member 706b distally with respect to first elongate member 706a.

Once a medical procedure is complete, the user may return anchor portion 702 to either contracted configuration before withdrawing the anchor assembly from the tissue, thereby minimizing contact between anchor portion 702 and an external sheath or a tissue track as anchor assembly 700 is withdrawn.

Reference is now made to FIG. 9A, which illustrates an anchor assembly 900 according to another embodiment. Anchor assembly 900 is similar to anchor assembly 700 except that instead of including a plurality of wires, anchor portion 902 is comprised of a single wire 904, as shown in FIG. 9B. As shown in FIGS. 9A and 9B, wire 904 includes a plurality of sections 906 that loop back and forth longitudinally between distal end 714 of second elongate member 708a and cap 712. Each section includes a proximal loop 908 and a distal loop 910 that are respectively welded or otherwise affixed to second elongate member 706b and cap 712. In a similar manner to wires 716, sections 906 can also form projections 912 that are configured to have a deployed, expanded configuration, as shown in FIG. 8A, and one or more undeployed, contracted configurations, as shown in FIGS. 8B and 8C. Reference is now made to FIGS. 10A and 10B, which illustrates an anchor assembly 1000 according to another embodiment. Similar to anchor assembly 700, anchor assembly 1000 includes an anchor portion 1002 and first and second elongate members 1004a and 1004b. Also similar to anchor assembly 700, anchor portion 1002 includes a plurality of wires 1006 extending between second elongate member 1004b and a cap 1008. Wires 1006 also include projections 1010 that extend away from the longitudinal axis 1011 of elongate portions 1004. Projections 1010 are configured to have a deployed, expanded configuration, as shown in FIG. 10A, and an undeployed, contracted configuration, as shown in FIG. 10B.

However, instead of moving cap 1008 longitudinally to deploy and contract wires 1006, anchor assembly 1000 does so using a twisting motion. To accomplish this, wires 1006 are attached to second elongate member 1004b at a different location than wires 716. Second elongate member 1004b includes a distal portion 1012 that can have a smaller outer diameter than the rest of second elongate member 1004b. Distal portion 1012 extends proximally from distal end 1014 of second elongate member 1004b to a proximal end 1016. Similar to wires 716, each wire 1006 has a distal end 1018 that is welded or otherwise attached to cap 1008. However, unlike wires 716, each wire 1006 extends from distal end 1018 to a proximal end 1020 that is welded or otherwise attached to an outer surface 1022 of second elongate member 1004b at proximal end 1016 of reduced diameter distal portion 1012. Alternatively, wires 1006 can extend through second elongate member 1004b at proximal end 1016 of reduced diameter distal portion 1012 and attach to an inner surface 1024. As shown in FIGS. 10A and 10B, cap 1008 is positioned adjacent distal end 1014 of second elongate member 1004b in both configurations.

As shown in FIG. 10A, anchor portion 1002 of anchor assembly 1000 has an expanded configuration in which projections 1010 extend radially away from longitudinal axis 1011 of elongate members 1004. In one embodiment, the expanded configuration of anchor portion 1002 may be formed when elongate projections 1010 fold roughly upon themselves with the bend of each projection 1010 extending radially outward.

As shown in FIG. 10B, anchor portion 1002 also has a contracted configuration. In the contracted configuration, wires 1006 are twisted about second elongate member 1004b so as to contact or otherwise be adjacent to outer surface 1022 of distal portion 1012. This can be accomplished by rotating cap 1008 about longitudinal axis 1011 with respect to second elongate member 1004b, by rotating first elongate member 1004a as depicted by arrow 1026. Thus, instead of moving plunger member 106 (FIG. 1) longitudinally, plunger member 106 can instead be rotated to effect the movement of anchor assembly 1000 between the contracted and expanded configurations. Having anchor portion 1002 in the contracted configuration shown in FIG. 10B may facilitate the delivery of anchor assembly 1000 into a tissue opening or the retraction of anchor assembly 1000 from a tissue opening.

For example, a user may rotate first elongate member 1004a and maintain tension thereon as anchor assembly 1000 is advanced at least partially through the tissue opening. Thereafter, the user may release the tension on first elongate member 1004a, causing first elongate member 1004a to rotate in the opposite direction and causing anchor portion 1002 to move, perhaps superelastically, to the expanded configuration shown in FIG. 10A.

Once a medical procedure is complete, the user may return anchor portion 1002 to the contracted configuration before withdrawing the anchor assembly from the tissue, thereby minimizing contact between anchor portion 1002 and an external sheath or a tissue track as anchor assembly 1000 is withdrawn. In some embodiments first elongate member 1004a can be rotated clockwise to move anchor assembly to the contracted position; in other embodiments first elongate member 1004a can be rotated counterclockwise to move anchor assembly to the contracted position; and in other embodiments, first elongate member 1004a can be rotated in either direction to move anchor assembly to the contracted position. In the depicted embodiment, each anchor portion 1002 is comprised of a plurality of wires. It is appreciated that in other embodiments, anchor portion 1002 can be formed from a single wire.

Reference is now made to FIGS. 11A-11C, which illustrate an anchor assembly 1100 according to another embodiment. Anchor assembly 1100 is similar to anchor assembly 600 in that it too includes a plurality of anchor elements 1101 each having an elongate portion 1104 and an anchor portion 1102 radially extending therefrom. However, in anchor assembly 1100, each anchor element 1101 loops back on itself so that both ends of the anchor element constitute elongate portion 1104 and the middle section that loops back on itself constitutes the anchor portion 1102. That is, each anchor element 1101 has a first end portion 1106 and a second end portion 1108 that both extend proximally from opposing ends 1110 and 1112 of a middle portion 1114. First and second end portions 1106 and 1108 constitute elongate portion 1104.

In the deployed configuration shown in FIG. 11A, middle portion 1114 comprises a single wire extending from opposing ends 1110 and 1112 to an end loop 1116. The end loop 1116 is bent back proximally. As such, as shown in FIG. 11B a space 1118 is created between the inside surface 510 of tissue wall 506 and the non-looped section of middle portion 1114 when the end loop 1116 is positioned against the inside surface 510. This can be beneficial when using a closure element 514 in conjunction with anchor assembly 1100.

For example, as shown in FIG. 11B, the space 1118 between inside surface 510 of tissue wall 506 and middle portion 1114 allows tines 1120 of the closure element 514 to extend through tissue surface 510 while positioning closure element 514 without snagging or otherwise catching on the wires that constitute anchor assembly 1100. When anchor assembly 1100 moves to the undeployed configuration shown in FIG. 11C, closure element 514 is already in position on tissue wall 506 so that the anchor elements 1101 will not likely snag or otherwise catch on tines 1120 or any other portion of closure element 514. In the depicted embodiment, each anchor element 1101 is comprised of a separate wire. It is appreciated that in other embodiments, anchor elements 1101 can be coupled together so as to be formed from a single wire.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method of closing an opening in a tissue wall having a proximal surface and an opposing distal surface, the method comprising:
    deploying an anchor assembly, the anchor assembly comprising an anchor portion and an elongate portion, the anchor portion comprising one or more anchor sections configured to move from an initial contracted configuration to a deployed expanded configuration upon deployment of the anchor assembly, a proximal end of the anchor sections being mounted to an elongate member and a distal end of the anchor sections being mounted to a distal cap mounted to the elongate portion, the anchor portion comprises a first undulating section and a second undulating section, the first undulating section having a first end, a proximal loop, and a distal loop, the second undulating section having a second end, a proximal loop, and a distal loop, the first end of the first undulating section is connected to the second end of the second undulating section such that the first undulating section and the second undulating section form a stepped distal end of the anchor portion with the first undulating section and the second undulating section extending circumferentially around the elongate portion in a sinuous path;
    positioning each of the anchor sections of the anchor portion against the distal surface of the tissue wall proximate the opening;
    deploying a closure element to close the opening in the tissue wall, the anchor sections of the anchor portion remaining positioned against the distal surface of the tissue wall during deployment of the closure element; and
    retracting the anchor sections of the anchor portion.

2. The method of claim 1, wherein the anchor sections are withdrawn through the closure element during retraction of the anchor sections.

3. The method of claim 1, wherein the anchor sections move from the deployed expanded configuration back to the initial contracted configuration during retraction of the anchor sections.

4. The method of claim 1, wherein the proximal loop of the first undulating section is independent from the proximal loop of the second undulating section.

5. A method of closing an opening in a tissue wall having a proximal surface and an opposing distal surface, the method comprising:
    deploying an anchor assembly against a distal surface of the tissue wall to sandwich the tissue wall proximate the opening between the anchor assembly and a tube set comprising a first tube and a second tube within the first tube, the anchor assembly comprising an anchor portion and an elongate portion, the anchor portion comprising one or more anchor sections configured to move from an initial contracted configuration to a deployed expanded configuration upon deployment of the anchor assembly, a proximal end of each of the one or more anchor sections being attached to the second tube, wherein the anchor portion comprises a first undulating section connected to a second undulating section such that the first undulating section and the second undulating section form a stepped distal end of the anchor portion, the first undulating section and the second undulating section extending circumferentially around the elongate portion, which extends through the tube set, in a sinuous path;
    deploying a closure element from between the first tube and the second tube to close the opening in the tissue wall, the anchor sections of the anchor portion remaining positioned against the distal surface of the tissue wall during deployment of the closure element;
    retracting the anchor sections of the anchor portion back into the tube set; and
    removing the anchor assembly from the closed opening.

6. The method of claim 5, further comprising inserting a portion of the tube set through the opening.

7. The method of claim 5, wherein a distal end of the tube set remains positioned against the proximal surface of the tissue wall during deployment of the closure element.

8. The method of claim 5, wherein a distal end of the tube set remains positioned against the proximal surface of the tissue wall during retraction of the anchor sections back into the tube set.

9. The method of claim 5, wherein the anchor sections are withdrawn through the closure element during retraction of the anchor sections back into the tube set.

10. The method of claim 5, wherein the anchor sections move from the deployed expanded configuration back to the initial contracted configuration during retraction of the anchor sections back into the tube set.

11. A method of closing an opening in a tissue wall having a proximal surface and an opposing distal surface, the method comprising:
    positioning a closure system adjacent to the opening in the tissue wall, the closure system including an anchor assembly and a closure element disposed within a tube set;
    deploying the anchor assembly, the anchor assembly comprising an anchor portion and an elongate portion, the anchor portion comprising one or more anchor sections configured to move from an initial contracted configuration to a deployed expanded configuration upon deployment of the anchor assembly, a proximal end of the anchor sections being mounted to an elongate member and a distal end of the anchor sections being mounted to a distal cap mounted to the elongate portion, wherein the anchor portion comprises a first undulating section connected to a second undulating section such that the first undulating section and the second undulating section form a stepped distal end of the anchor portion, the first undulating section and the second undulating section extending circumferentially around the elongate portion, which extends through the tube set, in a sinuous path;

positioning each of the anchor sections of the anchor portion against the distal surface of the tissue wall proximate the opening;

positioning a distal end of the tube set against the proximal surface of the tissue wall proximate the opening to sandwich the tissue wall proximate the opening between the anchor sections and the tube set;

deploying the closure element to close the opening in the tissue wall, the anchor sections of the anchor portion remaining positioned against the distal surface of the tissue wall during deployment of the closure element;

retracting the anchor sections of the anchor portion back into the tube set; and removing the closure system from the closed opening.

12. The method of claim 11, wherein positioning the closure system adjacent to the opening in the tissue wall comprises inserting a portion of the tube set through the opening.

13. The method of claim 11, wherein the distal end of the tube set remains positioned against the proximal surface of the tissue wall during deployment of the closure element.

14. The method of claim 11, wherein the distal end of the tube set remains positioned against the proximal surface of the tissue wall during retraction of the anchor sections back into the tube set.

15. The method of claim 11, wherein the anchor sections are withdrawn through the closure element during retraction of the anchor sections back into the tube set.

16. The method of claim 11, wherein the anchor sections move from the deployed expanded configuration back to the initial contracted configuration during retraction of the anchor sections back into the tube set.

\* \* \* \* \*